United States Patent
Forsell

(10) Patent No.: US 8,556,796 B2
(45) Date of Patent: *Oct. 15, 2013

(54) CONTROLLED URINARY INCONTINENCE TREATMENT

(75) Inventor: Peter Forsell, Bouveret (CH)

(73) Assignee: Obtech Medical AG, Baar (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/688,375

(22) Filed: Jan. 15, 2010

(65) Prior Publication Data

US 2010/0145139 A1    Jun. 10, 2010

Related U.S. Application Data

(63) Continuation of application No. 10/203,094, filed as application No. PCT/SE01/00252 on Feb. 8, 2001, now Pat. No. 7,648,455.

(60) Provisional application No. 60/181,465, filed on Feb. 10, 2000, provisional application No. 60/181,466, filed on Feb. 10, 2000.

(51) Int. Cl.
    *A61F 2/02* (2006.01)
(52) U.S. Cl.
    USPC .......................................... 600/30
(58) Field of Classification Search
    USPC .......................................... 600/38–41, 28–31
    See application file for complete search history.

(56) References Cited

U.S. PATENT DOCUMENTS

| 2,060,913 A | 11/1936 | Weaver |
| 2,795,641 A | 6/1957 | Ross |
| 3,209,081 A | 9/1965 | Ducote et al. |
| 3,598,287 A | 8/1971 | De Man |
| 3,662,758 A | 5/1972 | Glover |
| 3,692,027 A | 9/1972 | Ellinwood, Jr. |
| 3,705,575 A | 12/1972 | Edwards |
| 3,731,679 A | 5/1973 | Wilhelmson et al. |
| 3,731,681 A | 5/1973 | Blackshear et al. |
| 3,750,194 A | 8/1973 | Summers |
| 3,817,237 A | 6/1974 | Bolduc |
| 3,855,122 A | 12/1974 | Bourganel |
| 3,863,622 A | 2/1975 | Buuck |

(Continued)

FOREIGN PATENT DOCUMENTS

| CN | 104 74 47 | 12/1990 |
| CN | 227 58 59 | 3/1998 |

(Continued)

OTHER PUBLICATIONS

U.S. Appl. No. 12/656,513, Forsell Feb. 1, 2010.*

(Continued)

*Primary Examiner* — Samuel G Gilbert
(74) *Attorney, Agent, or Firm* — Nixon & Vanderhye, P.C.

(57) ABSTRACT

A urinary incontinence treatment apparatus comprises a restriction device implantable in a patient, for engaging the urethra or urine bladder to form a restricted urine passageway in the urethra or urine bladder. The restriction device is operable by an implantable operation device to change the restriction of the urine passageway. A control device is provided for controlling a source of energy, which may or may not be implanted, from outside the patient's body, to release energy for use in connection with the operation of the restriction device, i.e. to power the operation device.

142 Claims, 7 Drawing Sheets

(56) References Cited

U.S. PATENT DOCUMENTS

| | | |
|---|---|---|
| 3,875,928 A | 4/1975 | Angelchik |
| 3,906,674 A | 9/1975 | Stone |
| 3,923,060 A | 12/1975 | Ellinwood, Jr. |
| 3,954,102 A | 5/1976 | Buuck |
| 4,003,379 A | 1/1977 | Ellinwood, Jr. |
| 4,009,711 A | 3/1977 | Uson |
| 4,026,305 A | 5/1977 | Brownlee et al. |
| 4,044,401 A | 8/1977 | Guiset |
| 4,146,029 A | 3/1979 | Ellinwood, Jr. |
| 4,190,040 A | 2/1980 | Schulte |
| 4,201,202 A | 5/1980 | Finney et al. |
| 4,221,219 A | 9/1980 | Tucker |
| 4,235,222 A | 11/1980 | Ionescu |
| 4,243,306 A | 1/1981 | Bononi |
| 4,246,893 A | 1/1981 | Berson |
| 4,265,241 A | 5/1981 | Portner et al. |
| 4,271,827 A | 6/1981 | Angelchik |
| 4,274,407 A | 6/1981 | Scarlett |
| 4,304,225 A | 12/1981 | Freeman |
| 4,318,396 A | 3/1982 | Finney |
| 4,342,308 A | 8/1982 | Trick |
| 4,369,771 A | 1/1983 | Trick |
| 4,400,169 A | 8/1983 | Stephen |
| 4,408,597 A | 10/1983 | Tenney, Jr. |
| 4,412,530 A | 11/1983 | Burton |
| 4,424,807 A | 1/1984 | Evans |
| 4,426,893 A | 1/1984 | Miller |
| 4,456,175 A | 6/1984 | Mamrosov et al. |
| 4,464,628 A | 8/1984 | Nozawa |
| 4,491,461 A | 1/1985 | Hoekstra |
| 4,505,710 A | 3/1985 | Collins |
| 4,509,947 A | 4/1985 | Lattin |
| 4,538,607 A | 9/1985 | Saul |
| 4,542,753 A | 9/1985 | Brenman et al. |
| 4,550,720 A | 11/1985 | Trick |
| 4,556,050 A | 12/1985 | Hodgson et al. |
| 4,559,930 A | 12/1985 | Cobiski |
| 4,559,931 A | 12/1985 | Fischell |
| 4,563,175 A | 1/1986 | LaFond |
| 4,568,851 A | 2/1986 | Soni et al. |
| 4,583,523 A | 4/1986 | Kleinke et al. |
| 4,584,994 A | 4/1986 | Bamberger et al. |
| 4,592,339 A | 6/1986 | Kuzmak et al. |
| 4,592,355 A | 6/1986 | Antebi |
| 4,599,081 A | 7/1986 | Cohen |
| 4,602,621 A | 7/1986 | Hakky |
| 4,610,658 A | 9/1986 | Buchwald et al. |
| 4,623,350 A | 11/1986 | Lapeyre et al. |
| 4,628,928 A | 12/1986 | Lowell |
| 4,634,443 A | 1/1987 | Haber |
| 4,664,100 A | 5/1987 | Rudloff |
| 4,677,534 A | 6/1987 | Okochi |
| 4,679,560 A | 7/1987 | Galbraith |
| 4,696,288 A | 9/1987 | Kuzmak et al. |
| 4,711,231 A | 12/1987 | Finegold et al. |
| 4,723,538 A | 2/1988 | Stewart et al. |
| 4,756,949 A | 7/1988 | Spence et al. |
| 4,771,772 A | 9/1988 | DeWitt |
| 4,771,780 A | 9/1988 | Sholder |
| 4,773,403 A | 9/1988 | Daly |
| 4,780,064 A | 10/1988 | Olsen |
| 4,822,341 A | 4/1989 | Colone |
| 4,828,544 A | 5/1989 | Lane et al. |
| 4,828,990 A | 5/1989 | Higashi et al. |
| 4,829,990 A | 5/1989 | Thuroff et al. |
| 4,846,794 A | 7/1989 | Hertzer |
| 4,902,279 A | 2/1990 | Schmidtz et al. |
| 4,925,443 A | 5/1990 | Heilman et al. |
| 4,941,461 A | 7/1990 | Fischell |
| 4,942,668 A | 7/1990 | Franklin |
| 4,950,224 A | 8/1990 | Gorsuch et al. |
| 4,958,630 A | 9/1990 | Rosenbluth et al. |
| 4,979,955 A | 12/1990 | Smith |
| 4,982,731 A | 1/1991 | Lue et al. |
| 4,983,177 A | 1/1991 | Wolf |
| 5,006,106 A | 4/1991 | Angelchik |
| 5,012,822 A | 5/1991 | Schwarz |
| 5,042,084 A | 8/1991 | Daly |
| 5,048,511 A | 9/1991 | Rosenbluth et al. |
| 5,057,075 A | 10/1991 | Moncrief et al. |
| 5,062,416 A | 11/1991 | Stucks |
| 5,074,868 A | 12/1991 | Kuzmak |
| 5,078,676 A | 1/1992 | Bailly |
| 5,098,369 A | 3/1992 | Heilman et al. |
| 5,112,202 A | 5/1992 | Oshima et al. |
| 5,123,428 A | 6/1992 | Schwarz |
| 5,151,082 A | 9/1992 | Gorsuch et al. |
| 5,152,743 A | 10/1992 | Gorsuch et al. |
| 5,160,338 A | 11/1992 | Vincent |
| 5,194,145 A | 3/1993 | Schoendorfer |
| 5,224,926 A | 7/1993 | Gorsuch et al. |
| 5,226,429 A | 7/1993 | Kuzmak |
| 5,250,020 A | 10/1993 | Bley |
| 5,272,664 A | 12/1993 | Alexander |
| 5,297,536 A | 3/1994 | Wilk |
| 5,304,206 A | 4/1994 | Baker, Jr. et al. |
| 5,316,543 A | 5/1994 | Eberbach |
| 5,358,474 A | 10/1994 | Kaldany |
| 5,397,354 A | 3/1995 | Wilk et al. |
| 5,415,660 A | 5/1995 | Campbell et al. |
| 5,435,230 A | 7/1995 | Phillips |
| 5,437,605 A | 8/1995 | Helmy |
| 5,449,368 A | 9/1995 | Kuzmak |
| 5,453,079 A | 9/1995 | Schwaninger |
| 5,454,840 A | 10/1995 | Krakovsky et al. |
| 5,501,703 A | 3/1996 | Holsheimer et al. |
| 5,504,700 A | 4/1996 | Insley |
| 5,505,733 A | 4/1996 | Justin et al. |
| 5,509,888 A | 4/1996 | Miller |
| 5,518,499 A | 5/1996 | Aghr |
| 5,518,504 A | 5/1996 | Polyak |
| 5,531,684 A | 7/1996 | Ensminger et al. |
| 5,540,731 A | 7/1996 | Testerman |
| 5,562,598 A | 10/1996 | Whalen et al. |
| 5,569,187 A | 10/1996 | Kaiser |
| 5,578,069 A | 11/1996 | Miner, II |
| 5,582,580 A | 12/1996 | Buckman, Jr. et al. |
| 5,665,065 A | 9/1997 | Colman et al. |
| 5,676,674 A | 10/1997 | Bolanos et al. |
| 5,690,108 A | 11/1997 | Chakeres |
| 5,702,431 A | 12/1997 | Wang et al. |
| 5,704,893 A | 1/1998 | Timm |
| 5,704,915 A | 1/1998 | Melsky et al. |
| 5,735,809 A | 4/1998 | Gorsuch |
| 5,735,887 A | 4/1998 | Barreras et al. |
| 5,738,792 A | 4/1998 | Schoendorfer |
| 5,749,909 A | 5/1998 | Schroeppel et al. |
| 5,769,877 A | 6/1998 | Barreras |
| 5,771,903 A | 6/1998 | Jakobsson |
| 5,814,020 A | 9/1998 | Gross |
| 5,823,991 A | 10/1998 | Shim |
| 5,827,286 A | 10/1998 | Incavo et al. |
| 5,836,935 A | 11/1998 | Ashton et al. |
| 5,848,962 A | 12/1998 | Feindt et al. |
| 5,858,001 A | 1/1999 | Tsals et al. |
| 5,876,425 A | 3/1999 | Gord et al. |
| 5,900,909 A | 5/1999 | Parulski et al. |
| 5,902,336 A | 5/1999 | Mishkin |
| 5,910,149 A | 6/1999 | Kuzmak |
| 5,928,195 A | 7/1999 | Malamud et al. |
| 5,938,584 A | 8/1999 | Ardito et al. |
| 5,938,669 A | 8/1999 | Klaiber et al. |
| 5,954,715 A | 9/1999 | Harrington et al. |
| 5,964,789 A | 10/1999 | Karsdon |
| 5,978,712 A | 11/1999 | Suda et al. |
| 5,980,478 A | 11/1999 | Gorsuch et al. |
| 5,995,874 A | 11/1999 | Borza |
| 5,997,501 A | 12/1999 | Gross et al. |
| 6,003,736 A | 12/1999 | Ljunggren |
| 6,034,878 A | 3/2000 | Umemura |
| 6,067,991 A | 5/2000 | Forsell |
| 6,074,341 A | 6/2000 | Anderson et al. |
| 6,077,215 A | 6/2000 | Leysieffer |
| 6,095,968 A | 8/2000 | Snyders |

(56) References Cited

U.S. PATENT DOCUMENTS

| | | |
|---|---|---|
| 6,099,460 A | 8/2000 | Denker |
| 6,102,887 A | 8/2000 | Altman |
| 6,102,922 A | 8/2000 | Jakobsson et al. |
| 6,113,574 A | 9/2000 | Spinello |
| 6,116,193 A | 9/2000 | Goeckner |
| 6,117,067 A | 9/2000 | Gil-Vernet |
| 6,134,470 A | 10/2000 | Hartlaub |
| 6,135,945 A | 10/2000 | Sultan |
| 6,145,505 A | 11/2000 | Nikolchev et al. |
| 6,162,238 A | 12/2000 | Kaplan et al. |
| 6,185,452 B1 | 2/2001 | Schulman et al. |
| 6,197,055 B1 | 3/2001 | Matthews |
| 6,210,347 B1 | 4/2001 | Forsell |
| 6,215,727 B1 | 4/2001 | Parson |
| 6,221,060 B1 | 4/2001 | Willard |
| 6,233,474 B1 | 5/2001 | Lemelson |
| 6,275,737 B1 | 8/2001 | Mann |
| 6,302,910 B1 | 10/2001 | Yamazaki et al. |
| 6,319,191 B1 | 11/2001 | Sayet et al. |
| 6,321,282 B1 | 11/2001 | Horowitz |
| 6,332,466 B1 | 12/2001 | Yoon |
| 6,346,099 B1 | 2/2002 | Altman |
| 6,377,640 B2 | 4/2002 | Trans |
| 6,400,988 B1 | 6/2002 | Gurewitsch |
| 6,436,054 B1 | 8/2002 | Viola et al. |
| 6,450,173 B1 * | 9/2002 | Forsell ............ 128/899 |
| 6,450,946 B1 * | 9/2002 | Forsell ............ 600/37 |
| 6,453,907 B1 * | 9/2002 | Forsell ............ 128/899 |
| 6,454,698 B1 * | 9/2002 | Forsell ............ 600/30 |
| 6,454,699 B1 * | 9/2002 | Forsell ............ 600/30 |
| 6,454,700 B1 * | 9/2002 | Forsell ............ 600/37 |
| 6,454,701 B1 * | 9/2002 | Forsell ............ 600/37 |
| 6,456,883 B1 | 9/2002 | Torgerson et al. |
| 6,460,543 B1 | 10/2002 | Forsell |
| 6,461,292 B1 * | 10/2002 | Forsell ............ 600/31 |
| 6,461,293 B1 * | 10/2002 | Forsell ............ 600/37 |
| 6,463,935 B1 * | 10/2002 | Forsell ............ 128/899 |
| 6,464,628 B1 | 10/2002 | Forsell |
| 6,464,655 B1 | 10/2002 | Shahinpoor |
| 6,470,892 B1 | 10/2002 | Forsell |
| 6,471,635 B1 * | 10/2002 | Forsell ............ 600/30 |
| 6,471,688 B1 | 10/2002 | Harper et al. |
| 6,475,136 B1 | 11/2002 | Forsell |
| 6,480,946 B1 | 11/2002 | Tomishima |
| 6,482,145 B1 | 11/2002 | Forsell |
| 6,502,161 B1 | 12/2002 | Perego et al. |
| 6,503,189 B1 * | 1/2003 | Forsell ............ 600/29 |
| 6,516,282 B2 | 2/2003 | Hedlund |
| 6,571,127 B1 | 5/2003 | Ben-Haim et al. |
| 6,572,585 B2 | 6/2003 | Choi |
| 6,576,010 B2 | 6/2003 | Ulert et al. |
| 6,589,229 B1 | 7/2003 | Connelly et al. |
| 6,600,953 B2 | 7/2003 | Flesler et al. |
| 6,638,208 B1 | 10/2003 | Natarajan et al. |
| 6,638,303 B1 | 10/2003 | Campbell |
| 6,640,309 B2 | 10/2003 | Doblar |
| 6,650,943 B1 | 11/2003 | Whitehurst et al. |
| 6,659,936 B1 | 12/2003 | Furness et al. |
| 6,678,561 B2 | 1/2004 | Forsell |
| 6,689,085 B1 | 2/2004 | Rubenstein et al. |
| 6,709,385 B2 | 3/2004 | Forsell |
| 6,740,075 B2 | 5/2004 | Lebel et al. |
| 6,772,011 B2 | 8/2004 | Dolgin |
| 6,839,393 B1 | 1/2005 | Sidiropoulos |
| 6,862,479 B1 | 3/2005 | Whitehurst et al. |
| 6,895,280 B2 | 5/2005 | Meadows et al. |
| 6,911,002 B2 | 6/2005 | Fierro |
| 6,915,165 B2 | 7/2005 | Forsell |
| 6,928,338 B1 | 8/2005 | Buchser et al. |
| 6,929,625 B2 | 8/2005 | Bierman |
| 6,948,918 B2 | 9/2005 | Hansen |
| 6,953,429 B2 | 10/2005 | Forsell |
| 6,954,871 B2 | 10/2005 | Kuhn |
| 6,960,233 B1 | 11/2005 | Berg et al. |
| 6,979,351 B2 | 12/2005 | Forsell et al. |
| 7,003,684 B2 | 2/2006 | Chang |
| 7,011,624 B2 | 3/2006 | Forsell |
| 7,017,583 B2 * | 3/2006 | Forsell ............ 128/899 |
| 7,043,295 B2 | 5/2006 | Starkebaum |
| 7,066,922 B2 | 6/2006 | Angel et al. |
| 7,108,686 B2 | 9/2006 | Burke et al. |
| 7,165,153 B2 | 1/2007 | Vogt |
| 7,207,936 B2 | 4/2007 | Forsell |
| 7,214,233 B2 | 5/2007 | Gannoe et al. |
| 7,217,236 B2 | 5/2007 | Calderon et al. |
| 7,222,224 B2 | 5/2007 | Woo |
| 7,235,044 B2 | 6/2007 | Forsell |
| 7,238,165 B2 | 7/2007 | Vincent |
| 7,250,037 B2 | 7/2007 | Shermer et al. |
| 7,311,690 B2 | 12/2007 | Burnett |
| 7,313,639 B2 | 12/2007 | Perego et al. |
| 7,330,753 B2 | 2/2008 | Policker et al. |
| 7,338,437 B2 | 3/2008 | Forsell |
| 7,367,938 B2 | 5/2008 | Forsell |
| 7,371,208 B2 | 5/2008 | Forsell |
| 7,395,822 B1 | 7/2008 | Burton et al. |
| 7,407,479 B2 | 8/2008 | Forsell |
| 7,407,481 B2 | 8/2008 | Forsell |
| 7,442,165 B2 | 10/2008 | Forsell |
| 7,455,663 B2 | 11/2008 | Bikovsky |
| 7,569,050 B2 | 8/2009 | Moberg et al. |
| 7,621,863 B2 | 11/2009 | Forsell |
| 7,648,455 B2 | 1/2010 | Forsell |
| 7,666,132 B2 | 2/2010 | Forsell |
| 7,669,601 B2 | 3/2010 | Tal |
| 7,670,280 B2 | 3/2010 | Gloth |
| 7,844,342 B2 | 11/2010 | Dlugos et al. |
| 7,846,160 B2 | 12/2010 | Payne et al. |
| 7,931,582 B2 | 4/2011 | Forsell |
| 7,972,354 B2 | 7/2011 | Prestezog et al. |
| 7,987,853 B2 | 8/2011 | Swann et al. |
| 7,988,616 B2 | 8/2011 | Forsell |
| 7,991,476 B2 | 8/2011 | Nachum |
| 8,070,768 B2 | 12/2011 | Kim et al. |
| 8,096,938 B2 | 1/2012 | Forsell |
| 8,096,939 B2 | 1/2012 | Forsell |
| 8,126,558 B2 | 2/2012 | Forsell |
| 8,195,296 B2 | 6/2012 | Longhini et al. |
| 8,287,444 B2 | 10/2012 | Forsell |
| 8,290,594 B2 | 10/2012 | Forsell |
| 8,313,423 B2 | 11/2012 | Forsell |
| 2001/0011543 A1 | 8/2001 | Forsell |
| 2001/0016738 A1 | 8/2001 | Harrington et al. |
| 2001/0041824 A1 | 11/2001 | Zappala |
| 2002/0022759 A1 | 2/2002 | Forsell |
| 2002/0028980 A1 | 3/2002 | Thierfelder et al. |
| 2002/0040208 A1 | 4/2002 | Flaherty et al. |
| 2002/0055711 A1 | 5/2002 | Lavi et al. |
| 2002/0072698 A1 | 6/2002 | Chiang et al. |
| 2002/0072759 A1 | 6/2002 | Fry |
| 2002/0095139 A1 | 7/2002 | Keogh et al. |
| 2002/0095164 A1 | 7/2002 | Andreas et al. |
| 2002/0120219 A1 | 8/2002 | Hovland et al. |
| 2002/0151922 A1 | 10/2002 | Hogendijk et al. |
| 2002/0165575 A1 | 11/2002 | Saleh |
| 2002/0183588 A1 | 12/2002 | Fierro |
| 2003/0009201 A1 | 1/2003 | Forsell |
| 2003/0009221 A1 | 1/2003 | Forsell |
| 2003/0014010 A1 | 1/2003 | Carpenter et al. |
| 2003/0014086 A1 | 1/2003 | Sharma |
| 2003/0021822 A1 | 1/2003 | Lloyd |
| 2003/0032855 A1 | 2/2003 | Shahinpoor |
| 2003/0032857 A1 | 2/2003 | Forsell |
| 2003/0050591 A1 | 3/2003 | Patrick McHale |
| 2003/0055442 A1 | 3/2003 | Laufer et al. |
| 2003/0060893 A1 | 3/2003 | Forsell |
| 2003/0066536 A1 | 4/2003 | Forsell |
| 2003/0069547 A1 | 4/2003 | Gonon |
| 2003/0088148 A1 | 5/2003 | Forsell |
| 2003/0092962 A1 | 5/2003 | Forsell |
| 2003/0100929 A1 | 5/2003 | Forsell |
| 2003/0105385 A1 | 6/2003 | Forsell |
| 2003/0109771 A1 | 6/2003 | Forsell |
| 2003/0125768 A1 | 7/2003 | Forsell |

(56) References Cited

U.S. PATENT DOCUMENTS

| | | |
|---|---|---|
| 2003/0144575 A1 | 7/2003 | Forsell |
| 2003/0144648 A1 | 7/2003 | Forsell |
| 2003/0163029 A1 | 8/2003 | Sonnenschein et al. |
| 2003/0200407 A1 | 10/2003 | Osaka |
| 2003/0208247 A1 | 11/2003 | Spinelli et al. |
| 2003/0231543 A1 | 12/2003 | Matsui |
| 2003/0233143 A1 | 12/2003 | Gharib et al. |
| 2004/0015041 A1 | 1/2004 | Melvin |
| 2004/0024285 A1 | 2/2004 | Muckter |
| 2004/0024419 A1 | 2/2004 | Slepian et al. |
| 2004/0034275 A1 | 2/2004 | Forsell |
| 2004/0068299 A1 | 4/2004 | Laske et al. |
| 2004/0089313 A1 | 5/2004 | Utley et al. |
| 2004/0098113 A1 | 5/2004 | Forsell et al. |
| 2004/0098545 A1 | 5/2004 | Pline et al. |
| 2004/0102804 A1 | 5/2004 | Chin |
| 2004/0122526 A1 | 6/2004 | Imran |
| 2004/0122527 A1 | 6/2004 | Imran |
| 2004/0147871 A1 | 7/2004 | Burnett |
| 2004/0162568 A1 | 8/2004 | Saadat et al. |
| 2004/0177918 A1 | 9/2004 | Murata et al. |
| 2004/0230718 A1 | 11/2004 | Polzin et al. |
| 2004/0236877 A1 | 11/2004 | Burton |
| 2004/0249451 A1 | 12/2004 | Lu et al. |
| 2004/0260316 A1 | 12/2004 | Knudson et al. |
| 2005/0009178 A1 | 1/2005 | Yost et al. |
| 2005/0038484 A1 | 2/2005 | Knudson et al. |
| 2005/0055025 A1 | 3/2005 | Zacouto et al. |
| 2005/0060030 A1 | 3/2005 | Lashinski et al. |
| 2005/0075697 A1 | 4/2005 | Olson et al. |
| 2005/0209633 A1 | 9/2005 | Callister et al. |
| 2005/0222678 A1 | 10/2005 | Lashinski et al. |
| 2005/0238506 A1 | 10/2005 | Mescher et al. |
| 2005/0240229 A1 | 10/2005 | Whitehurst et al. |
| 2005/0245957 A1 | 11/2005 | Starkebaum et al. |
| 2005/0261712 A1 | 11/2005 | Balbierz et al. |
| 2005/0266042 A1 | 12/2005 | Tseng |
| 2005/0267405 A1 | 12/2005 | Shah |
| 2005/0267596 A1 | 12/2005 | Chen et al. |
| 2005/0276261 A1 | 12/2005 | Kim |
| 2006/0025855 A1 | 2/2006 | Lashinski et al. |
| 2006/0034358 A1 | 2/2006 | Okamura |
| 2006/0069414 A1 | 3/2006 | Imran et al. |
| 2006/0083899 A1 | 4/2006 | Burazin et al. |
| 2006/0127246 A1 | 6/2006 | Forsell |
| 2006/0129028 A1 | 6/2006 | Krakousky |
| 2006/0142635 A1 | 6/2006 | Forsell |
| 2006/0149124 A1 | 7/2006 | Forsell |
| 2006/0149129 A1 | 7/2006 | Watts et al. |
| 2006/0161217 A1 | 7/2006 | Jaax et al. |
| 2006/0167539 A1 | 7/2006 | McEwan |
| 2006/0212055 A1 | 9/2006 | Karabey et al. |
| 2006/0224177 A1 | 10/2006 | Finitsis |
| 2006/0229688 A1 | 10/2006 | McClure et al. |
| 2006/0235482 A1 | 10/2006 | Forsell |
| 2006/0257446 A1 | 11/2006 | Tropsha et al. |
| 2007/0015959 A1 | 1/2007 | Forsell |
| 2007/0038232 A1 | 2/2007 | Kraemer |
| 2007/0038831 A1 | 2/2007 | Kim |
| 2007/0049790 A1 | 3/2007 | Wagner et al. |
| 2007/0073099 A1 | 3/2007 | Forsell |
| 2007/0092862 A1 | 4/2007 | Gerber |
| 2007/0109019 A1 | 5/2007 | Wu |
| 2007/0121389 A1 | 5/2007 | Wu |
| 2007/0156204 A1 | 7/2007 | Denker et al. |
| 2007/0162670 A1 | 7/2007 | Yang |
| 2007/0167670 A1 | 7/2007 | Coleman et al. |
| 2007/0193632 A1 | 8/2007 | Shu |
| 2007/0204924 A1 | 9/2007 | Delgiacco et al. |
| 2007/0225802 A1 | 9/2007 | Forsell |
| 2007/0232848 A1 | 10/2007 | Forsell |
| 2007/0233019 A1 | 10/2007 | Forsell |
| 2007/0250020 A1 | 10/2007 | Kim et al. |
| 2007/0265675 A1 | 11/2007 | Lund et al. |
| 2008/0004487 A1 | 1/2008 | Haverfield |
| 2008/0045783 A1 | 2/2008 | Forsell |
| 2008/0051718 A1 | 2/2008 | Kavazov et al. |
| 2008/0086179 A1 | 4/2008 | Sharma |
| 2008/0103544 A1 | 5/2008 | Weiner |
| 2008/0139873 A1 | 6/2008 | Peters et al. |
| 2008/0154256 A1 | 6/2008 | Payne et al. |
| 2008/0178889 A1 | 7/2008 | Tal |
| 2008/0200753 A1 | 8/2008 | Forsell |
| 2008/0214888 A1 | 9/2008 | Ben Shalom |
| 2008/0245371 A1 | 10/2008 | Gruber |
| 2008/0269548 A1 | 10/2008 | Vecchiotti et al. |
| 2008/0275296 A1 | 11/2008 | Forsell |
| 2009/0018388 A1 | 1/2009 | Forsell |
| 2009/0024108 A1 | 1/2009 | Lee-Sepsick et al. |
| 2009/0054725 A1 | 2/2009 | Forsell |
| 2009/0082705 A1 | 3/2009 | Asfora |
| 2009/0131959 A1 | 5/2009 | Rolland |
| 2009/0240100 A1 | 9/2009 | Forsell |
| 2009/0240294 A1 | 9/2009 | Forsell |
| 2009/0247817 A1 | 10/2009 | Forsell |
| 2009/0247818 A1 | 10/2009 | Forsell |
| 2009/0248033 A1 | 10/2009 | Forsell |
| 2009/0250068 A1 | 10/2009 | Forsell |
| 2009/0254106 A1 | 10/2009 | Forsell |
| 2009/0266366 A1 | 10/2009 | Swann et al. |
| 2010/0145139 A1 | 6/2010 | Forsell |
| 2010/0217067 A1 | 8/2010 | Forsell |
| 2010/0286735 A1 | 11/2010 | Garfield et al. |
| 2010/0305656 A1 | 12/2010 | Imran et al. |
| 2010/0312047 A1 | 12/2010 | Forsell |
| 2010/0312048 A1 | 12/2010 | Forsell |
| 2010/0312049 A1 | 12/2010 | Forsell |
| 2010/0312050 A1 | 12/2010 | Forsell |
| 2010/0312163 A1 | 12/2010 | Forsell |
| 2010/0312164 A1 | 12/2010 | Forsell |
| 2010/0312356 A1 | 12/2010 | Forsell |
| 2010/0318116 A1 | 12/2010 | Forsell |
| 2010/0318117 A1 | 12/2010 | Forsell |
| 2010/0318118 A1 | 12/2010 | Tal |
| 2010/0324360 A1 | 12/2010 | Forsell |
| 2010/0324361 A1 | 12/2010 | Forsell |
| 2010/0324362 A1 | 12/2010 | Forsell |
| 2010/0324591 A1 | 12/2010 | Forsell |
| 2010/0331614 A1 | 12/2010 | Forsell |
| 2010/0331615 A1 | 12/2010 | Forsell |
| 2010/0331616 A1 | 12/2010 | Forsell |
| 2010/0331617 A1 | 12/2010 | Forsell |
| 2010/0331945 A1 | 12/2010 | Forsell |
| 2010/0332000 A1 | 12/2010 | Forsell |
| 2011/0009894 A1 | 1/2011 | Forsell |
| 2011/0009896 A1 | 1/2011 | Forsell |
| 2011/0009897 A1 | 1/2011 | Forsell |
| 2011/0015473 A1 | 1/2011 | Forsell |
| 2011/0015474 A1 | 1/2011 | Forsell |
| 2011/0040143 A1 | 2/2011 | Forsell |
| 2011/0066254 A1 | 3/2011 | Forsell |
| 2011/0087337 A1 | 4/2011 | Forsell |
| 2011/0172693 A1 | 7/2011 | Forsell |
| 2011/0184230 A1 | 7/2011 | Forsell |
| 2011/0196505 A1 | 8/2011 | Forsell |
| 2011/0196506 A1 | 8/2011 | Forsell |
| 2012/0029550 A1 | 2/2012 | Forsell |

FOREIGN PATENT DOCUMENTS

| | | |
|---|---|---|
| DE | 19511998 | 10/1996 |
| EP | 0102548 | 3/1984 |
| EP | 01 343 40 | 3/1985 |
| EP | 0 200 286 | 11/1986 |
| EP | 0 252 258 A1 | 1/1988 |
| EP | 0300552 | 1/1989 |
| EP | 0378251 | 7/1990 |
| EP | 0412191 | 2/1991 |
| EP | 0 532 162 A1 | 3/1993 |
| EP | 0 583 012 | 2/1994 |
| EP | 0611561 | 9/1994 |
| EP | 0626154 | 11/1994 |
| EP | 0876808 | 11/1998 |
| EP | 1 004 330 | 5/2000 |

(56) References Cited

FOREIGN PATENT DOCUMENTS

| | | |
|---|---|---|
| EP | 1 033 142 | 9/2000 |
| EP | 1 072 238 | 1/2001 |
| EP | 1 514 526 | 3/2005 |
| EP | 1563814 | 8/2005 |
| EP | 1563866 | 8/2005 |
| EP | 1563886 | 8/2005 |
| EP | 1 586 283 | 10/2005 |
| EP | 1598030 | 11/2005 |
| EP | 1 681 041 | 7/2006 |
| EP | 1 878 452 | 1/2008 |
| EP | 1 884 259 A1 | 2/2008 |
| EP | 1 913 880 | 4/2008 |
| FR | 2688693 | 9/1993 |
| FR | 2692777 | 12/1993 |
| FR | 27565485 | 6/1998 |
| FR | 2797181 | 2/2001 |
| GB | 8 856 74 | 12/1961 |
| GB | 1194358 | 6/1970 |
| JP | 1-305945 | 12/1989 |
| JP | 2-211170 | 8/1990 |
| JP | 3-63047 | 3/1991 |
| JP | 3-158154 | 7/1991 |
| WO | WO 84/01282 | 4/1984 |
| WO | WO 91/00094 | 1/1991 |
| WO | WO 94/27504 | 12/1994 |
| WO | WO 96/01597 | 1/1996 |
| WO | WO 96/11036 | 4/1996 |
| WO | WO 96/39932 | 12/1996 |
| WO | WO 97/41799 | 11/1997 |
| WO | WO 98/06358 | 2/1998 |
| WO | WO 98/50099 | 11/1998 |
| WO | WO 99/18885 | 4/1999 |
| WO | WO 99/63907 | 12/1999 |
| WO | WO 00/09047 | 2/2000 |
| WO | WO 00/09048 | 2/2000 |
| WO | WO 00/15158 | 3/2000 |
| WO | WO 00/16686 | 3/2000 |
| WO | WO 00/33825 | 6/2000 |
| WO | WO 01/12078 | 2/2001 |
| WO | WO 01/12108 | 2/2001 |
| WO | WO 01/45487 | 6/2001 |
| WO | WO 01/45590 | 6/2001 |
| WO | WO 01/47431 | 7/2001 |
| WO | WO 01/47575 | 7/2001 |
| WO | WO 0147434 | 7/2001 |
| WO | WO 0147435 | 7/2001 |
| WO | WO 0147439 | 7/2001 |
| WO | WO 01/58391 | 8/2001 |
| WO | WO 0154615 | 8/2001 |
| WO | WO 01/67964 | 9/2001 |
| WO | WO 02/38217 | 5/2002 |
| WO | WO 02/40083 | 5/2002 |
| WO | WO 02/053210 | 7/2002 |
| WO | WO 02/058563 | 8/2002 |
| WO | WO 02/087657 | 11/2002 |
| WO | WO 02/100481 | 12/2002 |
| WO | WO 03/002192 | 1/2003 |
| WO | WO 03/033054 | 4/2003 |
| WO | WO 2004/012806 | 2/2004 |
| WO | WO 2004/018037 | 3/2004 |
| WO | WO 2004/019765 | 3/2004 |
| WO | WO 2004/060171 | 7/2004 |
| WO | WO 2004/071684 | 8/2004 |
| WO | WO 2004/101029 | 11/2004 |
| WO | WO 2005/072169 | 8/2005 |
| WO | WO 2005/105003 | 11/2005 |
| WO | WO 2006/114004 | 11/2006 |
| WO | WO 2006/122285 | 11/2006 |
| WO | WO 2006/134106 | 12/2006 |
| WO | WO 2007/017880 | 2/2007 |
| WO | WO 2007/041795 | 4/2007 |
| WO | WO 2007/051563 | 5/2007 |
| WO | WO 2007/109759 | 9/2007 |
| WO | WO 2007/137026 | 11/2007 |
| WO | WO 2007/149555 | 12/2007 |
| WO | WO 2008/135988 | 11/2008 |
| WO | WO 2009/010799 | 1/2009 |
| WO | WO 2009/096854 | 8/2009 |
| WO | WO 2009/096865 | 8/2009 |
| WO | WO 2009/096868 | 8/2009 |
| WO | WO 2009/115645 | 9/2009 |

OTHER PUBLICATIONS

U.S. Appl. No. 12/839,115, Forsell, Jul. 19, 2010.*
U.S. Appl. No. 12/839,162, Forsell, Jul. 19, 2010.*
U.S. Appl. No. 12/859,454, Forsell, Aug. 19, 2010.*
U.S. Appl. No. 12/758,684, Forsell Apr. 12, 2010.*
Publication No. EP 1568338A2, dated Aug. 31, 2005, for European Patent Application No. 05010107.0.
European Search Report, dated Sep. 14, 2006, for EP 05010107.0.
Examination Report, dated Nov. 4, 2008, in European Patent Application No. 05010107.0.
U.S. Appl. No. 09/373,224, filed Aug. 12, 1999, Forsell.
U.S. Appl. No. 11/988,450, filed May 27, 2009, Forsell.
Webster's II New River side University, 1984, pp. 573,1000.
Anand, SNEH. "Electrical Pacing of the Ampullary Isthmic Junction for Contraception", IEEE Engineering in Medicine & Biology $10^{TH}$ Annual International Conference, 1988.

* cited by examiner

CONTROLLED URINARY INCONTINENCE TREATMENT

This application is a Continuation Application of U.S. application Ser. No. 10/203,094, filed Oct. 16, 2002 now U.S. Pat. No. 7,648,455 which is the U.S. National Phase of International Application No. PCT/SE01/00252, filed Feb. 8, 2001, which designated the U.S., and which claims the benefit of Provisional Application Ser. No. 60/181,465, filed Feb. 10, 2000, and Provisional Application Ser. No. 60/181,466, filed Feb. 10, 2000, the entire contents of each of which are hereby incorporated by reference herein.

The present invention relates to a urinary incontinence treatment apparatus, comprising a restriction device implantable in a patient suffering from urinary incontinence for engaging the urethra or urine bladder to form a restricted urine passageway in the urethra or urine bladder, wherein the restriction device is operable to change the restriction of the urine passageway.

Urine incontinence is a widespread problem. Many people are helped through training of the muscles in the pelvic floor but too many have severe problems with urine leakage. Many different solutions to this problem have been tried. For example, there is a prior manually operated urine incontinence treatment apparatus having an artificial hydraulic sphincter device engaging the urethra and connected to an elastic reservoir implanted in the scrotum or in the region of the labia majora. A disadvantage of this prior apparatus is that over time hard fibrosis is developed around the reservoir which may cause malfunction of pumping components. Furthermore, it is a rather complicated task to manually squeeze the elastic implanted reservoir to pump hydraulic fluid to open the sphincter device when the patient needs to urinate. In particular women can get their fingers wet. The created fibrosis will sooner or later become a hard fibrotic layer, which may make it even more difficult to pump the reservoir. Yet a further disadvantage is that the use of hydraulic fluid always entails a risk of fluid leaking from implanted hydraulic components.

A prior hydraulic apparatus designed to compress the urethra is disclosed in U.S. Pat. No. 5,520,606. Prosthetic sphincters with an inflatable cuff, which surrounds the urethra or encloses it on two sides is disclosed in for example U.S. Pat. Nos. 4,571,749 and 4,222,377. U.S. Pat. No. 4,969,474 discloses a hydraulic method for treating both men and women with urinary incontinence problems in the same way. The apparatus of U.S. Pat. No. 4,969,474 includes a reservoir containing fluid and an inflatable compression means designed to compress urethra without risking tissue loss or necrosis to occur. An artificial hydraulically operated urethral sphincter employing an external magnet to achieve closure of the urethral cuff is disclosed in U.S. Pat. No. 5,562,598.

A prior mechanical prosthetic sphincter, disclosed in U.S. Pat. No. 4,619,245, comprises a manually controllable actuating component for implanting at a convenient location in the patients body.

The object of the present invention is to provide a new convenient urinary incontinence treatment apparatus, the performance of which may be affected by the patient at any time after operation, in particular when various needs arise over the course of a day, so that the patient substantially always is satisfied or comfortable.

This object is achieved by a urinary incontinence treatment apparatus of the kind stated initially, which is characterised in that a source of energy is provided, and a control device operable from outside the patient's body is provided for controlling the source of energy to release energy for use in connection with the operation of the restriction device, when the restriction device is implanted.

As a result, the advantage is achieved that the restriction device can be non-invasively operated, when the restriction device has to be adjusted. Furthermore, the apparatus of the invention provides a simple and effective control of the energy supplied to implanted components of the apparatus which ensures an extended and reliable functionality of the apparatus, possibly for the rest of the patient's life and at least many years.

The control device may also control the restriction device. The control device may comprise an internal control unit, preferably including a microprocessor, implantable in the patient for controlling the restriction device. The control device may further comprise an external control unit outside the patient's body, wherein the internal control unit is programmable by the external control unit, for example for controlling the restriction device over time. Alternatively, the internal control unit may control the restriction device over time in accordance with an activity schedule program, which may be adapted to the patient's needs.

A great advantage is that the patient is enabled to adjust the restriction of the urine passageway by using the control device whenever he likes during the day.

Conveniently, the external control unit may load the internal control unit with data in accordance with a loading mode only authorized for a doctor. For specialized controls of the restriction device, the external control unit may control the internal control unit in accordance with a doctor mode only authorized for the doctor. For simple controls of the restriction device, the external control unit may control the internal control unit in accordance with a patient mode permitted for the patient. Thus, by using the external control unit in accordance with different modes it is possible to have certain functions of the restriction device controlled by the patient and other more advanced functions controlled by the doctor, which enables a flexible post-operation treatment of the patient.

The control device may be adapted to control the source of energy to release energy, for instance to intermittently release energy in the form of a train of energy pulses, for direct use in connection with the operation of the restriction device. In accordance with a suitable embodiment the control device controls the source of energy to release electric energy, and the apparatus further comprises an implantable capacitor for producing the train of energy pulses from the released energy. In this case the term "direct" is used to mean, on one hand, that the released energy is used while it is being released by the control device, on the other hand, that the released energy may be somewhat delayed, in the order of seconds, by for instance an energy stabilizer before being used in connection with the operation of the restriction device. The restriction device may be operable in non-manual, a non-magnetic or non-mechanical manner by use of the released energy.

In accordance with a preferred embodiment of the invention, the apparatus comprises implantable electrical components including at least one, or only one single voltage level guard and a capacitor or accumulator, wherein the charge and discharge of the capacitor or accumulator is controlled by use of the voltage level guard. As a result, there is no need for any implanted current detector and/or charge level detector for the control of the capacitor, which makes the apparatus simple and reliable.

Generally, the apparatus further comprises an operation device implantable in the patient for operating the restriction device, wherein the control device controls the operation device to operate the restriction device. The control device may directly power the operation device with energy released from the source of energy and/or power other implantable energy consuming components of the apparatus. In this case the term "directly" is used to mean, on one hand, that the operation device is powered by released energy while the latter is being released by the control device, on the other hand, that the released energy may be somewhat delayed, in the order of seconds, by for instance an energy stabilizer before powering the operation device. The advantage of directly using energy as it is released is that the apparatus can be of a very simple design and the few components involved makes the apparatus reliable.

The control device may release magnetic, electromagnetic, kinetic, sonic or thermal energy, or non-magnetic, non-sonic, non-thermal, non-electromagnetic or non-kinetic energy.

However, preferably the operation device comprises an electrical operation device.

Typically the apparatus of the invention comprises an adjustment device for adjusting the restriction device to change the restriction of the urine passageway. The adjustment device may be adapted to mechanically adjust the restriction device. Alternatively, the adjustment device may be adapted to hydraulically adjust the restriction device by using hydraulic means which is devoid of hydraulic fluid of the kind having a viscosity that substantially increases when exposed to heat or a magnetic field, i.e. the hydraulic fluid would not become more viscous when exposed to heat or influenced by magnetic forces.

The restriction device may be non-inflatable, i.e. with no hydraulic fluid involved for the adjustments of the restriction device. This eliminates problems with fluid leaking from the restriction device.

The operation device may comprise hydraulic means and at least one valve for controlling a fluid flow in the hydraulic means. The control device may suitably comprise a wireless remote control for controlling the valve. The restriction device may comprise hydraulic means and the operation device may comprise a reservoir forming a fluid chamber with a variable volume connected to the hydraulic means. The operation device may distribute fluid from the chamber to the hydraulic means by reduction of the volume of the chamber and withdraw fluid from the hydraulic means to the chamber by expansion of the volume of the chamber.

In accordance with a first main aspect of the invention, the source of energy is external to the patient's body and the control device controls the source of energy to release wireless energy. The external source of energy may be of any conceivable kind, such as a nuclear source of energy or a chemical source of enemy.

An energy storage device, preferably an electric accumulator, may be implantable in the patient for storing the wireless energy released from the external source of energy. The electric accumulator may comprise at least one capacitor or at least one rechargeable battery, or a combination of at least one capacitor and at least one rechargeable battery. Alternatively, a battery may be implantable in the patient for supplying electric energy to implanted electric energy consuming components of the apparatus, in addition to the supply of wireless energy. Where the control device comprises implantable control unit the electronic circuit thereof and the restriction device may be directly powered by transformed wireless energy, or energy from either the implantable energy storage device or battery.

In accordance with a second main aspect of the invention, the wireless energy is directly used for operation of the restriction device, i.e. the restriction device is operated as the wireless energy is released from the external source of energy by the control device. In this case the term "directly" is used to mean, on one hand, that the restriction device is promptly operated by using the released energy without first storing the latter, on the other hand, that the released energy may be somewhat delayed, in the order of seconds, by for instance an energy stabilizer before being used for the operation of the restriction device. As a result, a very simple control of the restriction device is achieved and there are only a few implanted components of the apparatus. For example, there is no implanted source of energy, such as a battery, nor any implanted complicated signal control system. This gives the advantage that the apparatus will be extremely reliable.

Generally, the control device controls and directly or indirectly powers the operation device with wireless energy released from the source of energy and/or powers other implanted energy consuming components of the apparatus.

In a first particular embodiment in accordance with the first and second main aspects of the invention, the operation device comprises a motor, preferably an electric motor which may have electrically conductive parts made of plastics. The motor may include a rotary motor, wherein the control device is adapted to control the rotary motor to rotate a desired number of revolutions. Alternatively, the motor may include a linear motor, or a hydraulic or pneumatic fluid motor, wherein the control device is adapted to control the fluid flow through the fluid motor. Motors currently available on the market are getting smaller and smaller. Furthermore, there is a great variety of control methods and miniaturized control equipment available. For example, a number of revolutions of a rotary motor may be analyzed by a Hall-element just a few mm in size.

In a second particular embodiment in accordance with the first and second main aspects of the invention, the control device is adapted to shift polarity of the released energy to reverse the operation device. The operation device may suitably comprise an electric motor and the released energy may comprise electric energy.

In a third particular embodiment in accordance with the first and second main aspects of the invention, the restriction device is operable to perform a reversible function and there is a reversing device implantable in the patient for reversing the function performed by the restriction device. Such a reversing function preferably involves enlarging and restricting the urine passageway by the restriction device, suitably in a stepless manner. In this connection, the control device suitably controls the reversing device, which may include a switch, to reverse the function performed by the restriction device. The reversing device may comprise hydraulic means including a valve for shifting the flow direction of a fluid in the hydraulic means. Alternatively, the reversing device may comprise a mechanical reversing device, such as a switch or a gearbox.

Where the reversing device comprises a switch the control device suitably controls the operation of the switch by shifting polarity of released energy supplied to the switch. The switch may comprise an electric switch and the source of energy may supply electric energy for the operation of the switch. The switch mentioned above may comprise an electronic switch or, where applicable, a mechanical switch.

In accordance with the third particular embodiment, the operation device preferably comprises a motor, wherein the reversing device reverses the motor.

In a fourth particular embodiment in accordance with the first and second main aspects of the invention, the restriction device comprises hydraulic means, for example including an expansible/contractible cavity for fluid. Preferably, the operation device is adapted to conduct hydraulic fluid in the hydraulic means, and comprises a motor, a valveless fluid conduit connected to the hydraulic means of the restriction device, and a reservoir for fluid, wherein the reservoir forms part of the conduit. The operation device suitably comprises a pump operated by the motor. All of the hydraulic components involved are preferably devoid of any non-return valve. This is of great advantage, because with valves involved there is always a risk of malfunction due to improperly working valves, especially when long time periods passes between valve operations. The reservoir may form a fluid chamber with a variable volume, and the pump may distribute fluid from the chamber to the hydraulic means of the restriction device by reduction of the volume of the chamber and withdraw fluid from the hydraulic means to the chamber by expansion of the volume of the chamber.

In accordance with a third main aspect of the invention, the source of energy is implantable in the patient. Thus, when the source of energy is implanted in a patient the control device controls it from outside the patient's body to release energy. This solution is advantageous for embodiments of the apparatus that have a relatively high consumption of energy, which cannot be satisfied by direct supply of wireless energy.

The implantable source of energy may comprise an accumulator, preferably an electric source of energy, such as a battery having a lifetime of at least 10 years.

In accordance with a fourth main aspect of the invention, the apparatus comprises a switch implanted in the patient for directly or indirectly switching the operation of the restriction device and an internal source of energy, such as a battery, implanted in the patient for supplying energy for the operation of the restriction device, wherein the switch directly or indirectly affects the supply of energy from the internal source of energy. This solution is advantageous for embodiments of the apparatus that have a relatively high energy consumption which cannot be met by direct supply of wireless energy.

In a first particular embodiment in accordance with the fourth main aspect of the invention, the switch switches between an off mode, in which the internal source of energy is not in use, and an on mode, in which the internal source of energy supplies energy for the operation of the restriction device. In this case, the switch is conveniently operated by the wireless energy released from the external source of energy to switch between the on and off modes. The control device, preferably comprising a wireless remote control, may control the external source of energy to release the wireless energy. The advantage of this embodiment is that the lifetime of the implanted source of energy, such as a battery, can be significantly prolonged, since the implanted source of energy does not supply energy when the switch is in its off mode.

In a second particular embodiment in accordance with the fourth main aspect of the invention, the control device comprises a wireless remote control for controlling the internal source of energy. In this case, the switch is operable by the wireless energy from the external source of energy to switch between an off mode, in which the internal source of energy and remote control are not in use, and a standby mode, in which the remote control is permitted to control the internal source of energy to supply energy for the operation of the restriction device.

In a third particular embodiment in accordance with the fourth main aspect of the invention, the apparatus further comprises an energy transforming device implanted in the patient for transforming the wireless energy into storable energy, wherein the internal source of energy is capable of storing the storable energy. The internal source of energy preferably comprises an electric accumulator, at least one capacitor or at least one rechargeable battery, or a combination of at least one capacitor and at least one rechargeable battery. In this case, the switch switches from an off mode, in which the internal source of energy is not in use, to an on mode, in which the internal source of energy supplies energy for the operation of the restriction device.

The control device, preferably comprising a wireless remote control, may control the switch to switch between the on and off modes.

Alternatively, in this third particular embodiment an energy storage device may be implanted in the patient for storing the storable energy instead of the internal source of energy, wherein the switch is operable by energy from the implanted energy storage device to switch between an off mode, in which the internal source of energy is not in use, and an on mode, in which the internal source of energy supplies energy for the operation of the restriction device. In this case, the control device (the wireless remote control) controls the energy storage device to operate the switch.

The internal source of energy preferably comprises an electric source of energy, such as an accumulator or a battery having a lifetime of at least 10 years. However, other kinds of sources are also conceivable, such as a nuclear source of energy or a chemical source of energy.

The above first, second, third and fourth particular embodiments described in connection with the first and second main aspects of the invention are also applicable in accordance with the third main aspect of the invention, i.e. where the source of energy is implantable, and in accordance with the fourth main aspect of the invention, i.e. where the apparatus comprises an implantable switch.

All of the above embodiments may be combined with at least one implantable sensor for sensing at least one physical parameter of the patient, wherein the control device may control the restriction device in response to signals from the sensor. For example, the sensor may comprise a pressure sensor for directly or indirectly sensing the pressure in the urethra or urine bladder. The expression "indirectly sensing the pressure in the urethra or urine bladder" should be understood to encompass the cases where the sensor senses the pressure against the restriction device or human tissue of the patient. Where the control device comprises an internal control unit to be implanted in the patient, the internal control unit may suitably directly control the restriction device in response to signals from the sensor. In response to signals from the sensor, for example pressure, the patient's position or any other important physical parameter, the internal control unit may send information thereon to outside the patient's body. The control unit may also automatically control the restriction device in response to signals from the sensor. For example, the control unit may control the restriction device to firmly close the urine passageway in response to the sensor sensing that the patient is lying, or enlarge the urine passageway in response to the sensor sensing an abnormally high pressure against the restriction device.

Where the control device comprises an external control unit outside the patient's body, the external control unit may, suitably directly, control the restriction device in response to signals from the sensor. The external control unit may store information on the physical parameter sensed by the sensor and may be manually operated to control the restriction device based on the stored information. In addition, there may be at least one implantable sender for sending information on the physical parameter sensed by the sensor.

An external data communicator may be provided outside the patient's body and an internal data communicator to be implanted in the patient may be provided for communicating with the external data communicator. The internal data communicator may feed data related to the patient, or related to the restriction device, back to the external data communicator. Alternatively or in combination, the external data communicator may feed data to the internal data communicator. The internal data communicator may suitably feed data related to at least one physical signal of the patient.

Generally, the apparatus of the invention may comprise a switch implantable in the patient for directly or indirectly switching the energy released from the source of energy. For example, the restriction device may be operable to open and close the urine passageway or may steplessly control the restriction of the urine passageway. A pressure sensor may be provided for directly or indirectly sensing the pressure in the urethra or urine bladder. The control device may control the restriction device in response to signals from the pressure sensor.

The apparatus may comprise an implantable energy transforming device, wherein the control device releases electric energy and the energy transforming device transforms the electric energy into kinetic energy for, preferably direct, operation of the restriction device. Suitably, an implantable stabilizer, such as a capacitor or a rechargeable accumulator, or the like, may be provided for stabilizing the electric energy released by the control device. In addition, the control device may control the source of energy to release energy for a determined time period or in a determined number of energy pulses. Finally, the restriction device may be non-inflatable.

All of the above embodiments are preferably remote controlled. Thus, the control device advantageously comprises a wireless remote control transmitting at least one wireless control signal for controlling the restriction device. With such a remote control it will be possible to adapt the function of the apparatus to the patient's need in a daily basis, which is beneficial with respect to the treatment of the patient.

The wireless remote control may be capable of obtaining information on the condition of the restriction device and of controlling the restriction device in response to the information. Also, The remote control may be capable of sending information related to the restriction device from inside the patient's body to the outside thereof.

In a particular embodiment of the invention, the wireless remote control comprises at least one external signal transmitter or transceiver and at least one internal signal receiver or transceiver implantable in the patient. In another particular embodiment of the invention, the wireless remote control comprises at least one external signal receiver or transceiver and at least one internal signal transmitter or transceiver implantable the patient.

The remote control may transmit a carrier signal for carrying the control signal, wherein the carrier signal is frequency, amplitude or frequency and amplitude modulated and is digital, analog or digital and analog. Also the control signal used with the carrier signal may be frequency, amplitude or frequency and amplitude modulated.

The control signal may comprise a wave signal, for example, a sound wave signal, such as an ultrasound wave signal, an electromagnetic wave signal, such as an infrared light signal, a visible light signal, an ultra violet light signal, a laser signal, a micro wave signal, a radio wave signal, an x-ray radiation signal, or a gamma radiation signal. Where applicable, two or more of the above signals may be combined.

The control signal may be digital or analog, and may comprise an electric or magnetic field. Suitably, the wireless remote control may transmit an electromagnetic carrier wave signal for carrying the digital or analog control signal. For example, use of an analog carrier wave signal carrying a digital control signal would give safe communication. The control signal may be transmitted in pulses by the wireless remote control.

In all of the above solutions, the control device advantageously releases energy from the source of energy in a non-invasive, magnetic, non-magnetic, mechanical or non-mechanical manner.

The control device may release magnetic, electromagnetic, kinetic or thermal energy, or non-magnetic, non-thermal, non-electromagnetic or non-kinetic energy.

The control device may be activated in a manual or non-manual manner to control the source of energy to release energy.

The above-presented embodiments of the invention may be modified in accordance with the following suggestions. The released energy may comprise electric energy and an implantable capacitor having a capacity less than 0.1 µF may be provided for producing the above-mentioned train of energy pulses.

An implantable motor or pump may be provided for operating the restriction device, wherein the control device is adapted to control the source of energy to directly power the motor or pump with the released energy. Specifically, the control device may be adapted to release wireless energy in the form of a magnetic field or electromagnetic waves (excluding radio waves) for direct power of the motor or pump, as the wireless energy is being released. Where a pump is used it preferably is not a plunger type of pump.

Generally, the wireless energy comprises a signal.

The apparatus may further comprise implantable energy transforming device for transforming wireless energy directly or indirectly into energy different than the wireless energy, for operation of the restriction device. For example, the motor or pump may be powered by the transformed energy.

The energy transforming device may transform the wireless energy in the form of sound waves, preferably directly, into electric energy for operation of the restriction device. The energy transforming device may comprise a capacitor adapted to produce electric pulses from the transformed electric energy.

The motor mentioned in the present specification may also be directly powered with wirelessly transmitted electromagnetic or magnetic energy in the form of signals, as the energy is transmitted. Furthermore, all the various functions of the motor and associated components described in the present specification may be used where applicable.

Generally, the restriction device advantageously is embedded in a soft or gel-like material, such as a silicone material having hardness less than 20 Shore.

Of course, the restriction device preferably is adjustable in a non-manual manner.

All the above described various components, such as the motor, pump and capacitor, may be combined in the different embodiments where applicable. Also the various functions described in connection with the above embodiments of the invention may be used in different applications, where applicable.

All the various, ways of transferring energy and controlling the energy presented in the present specification may be practiced by using all of the various components and solutions described.

The present invention also provides methods for treating urinary incontinent patients.

Accordingly, in accordance with a first alternative method, there is provided a method of treating a patient suffering from urinary incontinence, comprising the steps of implanting an operable restriction device in the patient, so that the restriction device engages the urethra or urine bladder to form a restricted urine passageway in the urethra or urine bladder, providing a source of energy for energizing the restriction device, and controlling the source of energy to release energy for use in connection with the operation of the restriction device. The method may further comprise using energy released from the source of energy to operate the restriction device to open and close, respectively, the urine passageway.

In accordance with a second alternative method, there is provided a method of treating a patient suffering from urinary incontinence, comprising the steps of placing at least two laparascopical trocars in the patient's body, inserting a dissecting tool through the trocars and dissecting an area of the urethra or urine bladder, placing an operable restriction device in the dissected area, so that the restriction device engages the urethra or urine bladder to form a restricted urine passageway in the urethra or urine bladder, implanting a source of energy in the patient, and controlling the implanted source of energy from outside the patient's body to release energy for use in connection with the operation of the restriction device.

In accordance with a third alternative method, there is provided a method of treating a patient suffering from urinary incontinence, comprising: (a) Surgically implanting in the patient an operable restriction device engaging the patient's urethra or urine bladder to form a restricted urine passageway in the urethra or urine bladder. (b) Providing a source of energy external to the patient's body. (c) Controlling the external source of energy from outside the patient's body to release wireless energy. And (d) using the released wireless energy in connection with the operation of the restriction device.

The method may further comprise (e) implanting in the human or animal an operation device which can adjust the restricted urine passageway in response to supplied energy, and (f) using the released wireless energy to activate the implanted operation device so as (i) to enlarge the restricted urine passageway to allow urine to readily pass therethrough but normally restrict the urine passageway. In the method (f) may be practiced at least once a day, normally several times (e.g. 2-10) a day.

In accordance with a fourth alternative method, there is provided a method of treating a patient suffering from urinary incontinence, comprising the steps of placing at least two laparascopical trocars in the patient's body, inserting a dissecting tool through the trocars and dissecting an area of the urethra or urine bladder, placing an operable restriction device in the dissected area, so that the restriction device engages the urethra or urine bladder to form a restricted urine passageway in the urethra or urine bladder, providing an external source of energy outside the patient's body, controlling the external source of energy from outside the patient's body to release wireless energy, and using the released wireless energy in connection with the operation of the restriction device.

In accordance with a fifth alternative method, there is provided a method of treating a patient suffering from urinary incontinence, comprising the steps of placing at least two laparascopical trocars in the patient's body, inserting a dissecting tool through the trocars and dissecting an area of the urethra or urine bladder, implanting an operable restriction device in the dissected area, so that the restriction device engages the urethra or urine bladder to form a restricted urine passageway in the urethra or urine bladder, implanting an energy transforming device, providing an external source of energy, controlling the external source of energy to release wireless energy, and transforming the wireless energy by the energy transforming device into energy different than the wireless energy for use in connection with the operation of the restriction device. This method may further comprise implanting a stabilizer in the patient for stabilizing the energy transformed by the energy transforming device.

The invention is described in more detail in the following with reference to the accompanying drawings, in which FIGS. 1 to 6 are schematic block diagrams illustrating six embodiments, respectively, of the invention, in which wireless energy released from an external source of energy is used for direct operation of a restriction device engaging the urethra or urine bladder of a patient;

Referring to the drawing figures, like reference numerals designate identical or corresponding elements throughout the several figures.

Figure 1:
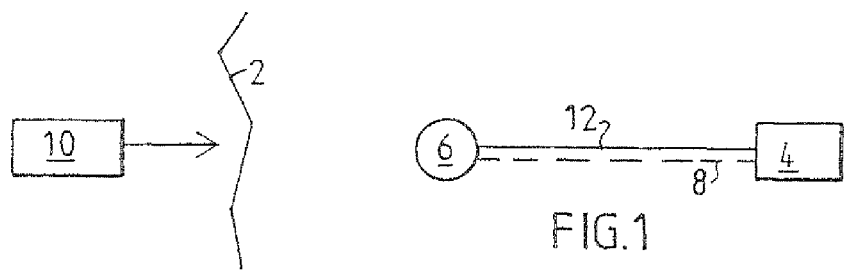

FIG. 1 schematically shows an embodiment of the urinary incontinence treatment apparatus of the invention having some parts implanted in a patient and other parts located, outside the patient's body. Thus, in FIG. 1 all parts placed to the right of the patient's skin 2 are implanted and all parts placed to the left of the skin 2 are located outside the patient's body. The apparatus of FIG. 1 comprises an implanted operable restriction device 4, which engages the patient's urethra (or alternatively the urine bladder) to form a restricted urine passageway. The restriction device 4 is capable of performing a reversible function, i.e. to open and close the urine passageway. An implanted control unit 6 controls the restriction device 4 via a control line 8 to form an adequate restriction of the of the urine passageway. An external control unit 10 includes an external source of energy and a wireless remote control transmitting a control signal generated by the external source of energy. The control signal is received by a signal receiver incorporated in the implanted control unit 6, whereby the control unit 6 controls the implanted restriction device 4 in response to the control signal. The implanted control unit 6 also uses energy from the control signal for operating the restriction device 4 via a power supply line 12.

Figure 2:
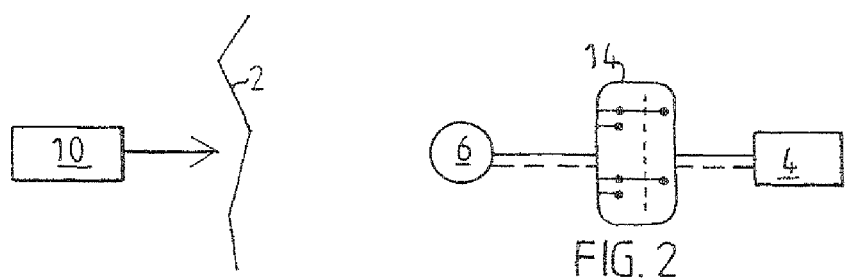

FIG. 2 shows an embodiment of the invention identical to that of FIG. 1, except that a reversing device in the form of a switch 14 operable by energy also is implanted in the patient for reversing the restriction device 4. The control unit 6 uses the switch 14 to reverse the function performed by the restriction device 4. More precisely, the external control unit 10 releases energy carried by a wireless signal and the implanted control unit 6 transforms the wireless energy into a current for operating the switch 14. When the control unit 6 shifts the polarity of the current the switch 14 reverses the function performed by the restriction device 4.

Figure 3:
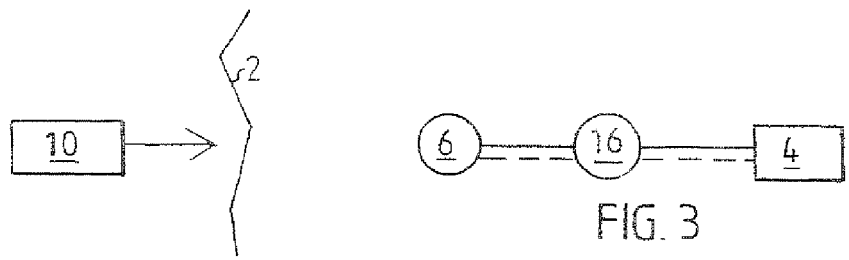

FIG. 3 shows an embodiment of the invention identical to that of FIG. 1, except that an operation device in the form of a motor 16 also is implanted in the patient. The implanted control unit 6 powers the motor 16 with wireless energy released from the external source of energy of the external control unit 10. The implanted control unit 6 controls the operation of the motor 16 in response to a control signal from the remote control of the external control unit 10.

Figure 4:
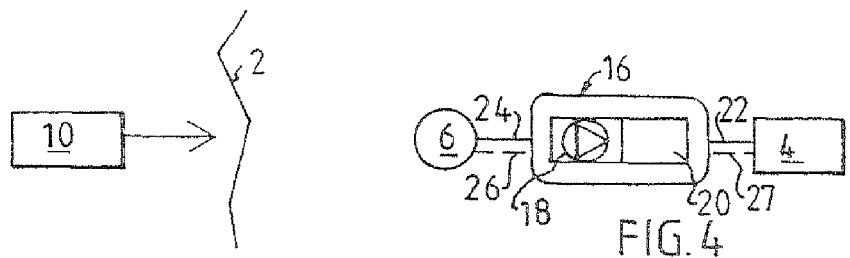

FIG. 4 shows an embodiment of the invention identical to that of FIG. 1, except that an assembly 16 including a motor/pump unit 18 and a fluid reservoir 20 also is implanted in the patient. In this case the restriction device 4 is hydraulically operated, i.e. hydraulic fluid is pumped by the motor/pump unit 18 from the reservoir 20 through a conduit 22 to the restriction device 4 to restrict the urine passageway, and hydraulic fluid is pumped by the motor/pump unit 18 back from the restriction device 4 to the reservoir 20 to enlarge the urine passageway. The external control unit 10 releases energy carried by a wireless signal and the implanted control unit 6 transforms the wireless energy into a current, for example a current, for powering the motor/pump unit 18 via an electric power supply line 24. The implanted control unit 6 controls the motor/pump unit 16 and the restriction device 4 via control lines 26 and 27.

Figure 5:
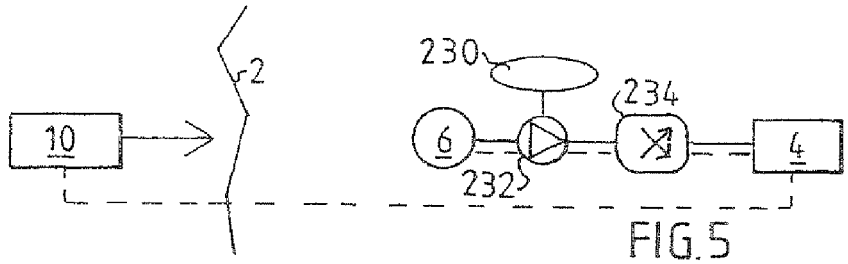

FIG. 5 shows an embodiment of the invention comprising the restriction device 4, hydraulically operated, and the implanted control unit 6, and further comprising a hydraulic fluid reservoir 230, a motor/pump unit 232 and a reversing device in the form of a hydraulic valve shifting device 234, all of which are implanted in the patient. The motor of the motor/pump unit 232 is an electric motor.

Figure 6:
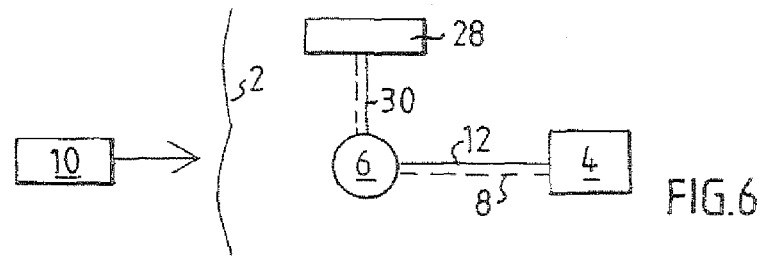

FIG. 6 shows an embodiment of the invention identical to that of FIG. 1, except that an accumulator 28 also is implanted in the patient. The control unit 6 stores energy received from the external control unit 10 in the accumulator 28. In response to a control signal from the external control unit 10 the implanted control unit 6 releases energy from the accumulator 28 via a power-line 30 for the operation of the restriction device 4.

Figure 7:
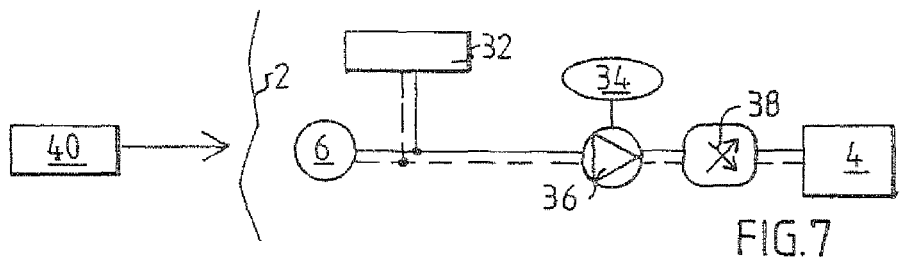
FIGS. 7 to 10 are schematic block diagrams illustrating four embodiments, respectively, of the invention, in which energy is released from an implanted source of energy.

FIG. 7 shows an embodiment of the invention comprising the restriction device 4, hydraulically operated, and the implanted control unit 6, and further comprising a source of energy in the form of a battery 32, a hydraulic fluid reservoir 34, a motor/pump unit 36 and a reversing device in the form of a hydraulic valve shifting device 38, all of which are implanted in the patient. The motor of the motor/pump unit 36 is an electric motor. An external control unit 40 includes a wireless remote control transmitting a control signal which is received by the signal receiver incorporated in the implanted control unit 6.

In response to a control signal from the external control unit 40 the implanted control unit 6 powers the motor/pump unit 36 with energy from the battery 32, whereby the motor/pump unit 36 distributes hydraulic fluid between the reservoir 34 and the restriction device 4. The control unit 6 controls the shifting device 38 to shift the hydraulic fluid flow direction between one direction in which the fluid is pumped by the motor/pump unit 36 from the reservoir 34 to the restriction device 4 to restrict the urine passageway, and another opposite direction in which the fluid is pumped by the motor/pump unit 36 back from the restriction device 4 to the reservoir 34 to enlarge the urine passageway.

Figure 8:
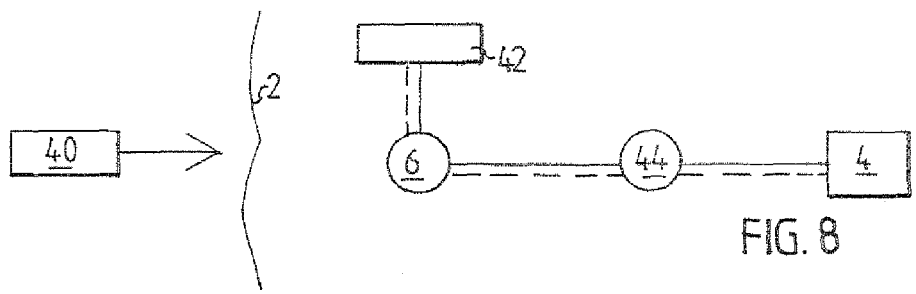

FIG. 8 shows an embodiment of the invention identical to that of FIG. 6, except that a battery 42 is substituted for the accumulator 28, the external control unit 40 of the embodiment of FIG. 5 is substituted for the external control unit 10 and an electric motor 44 is implanted in the patient for operating the restriction device 4. In response to a control signal from the external control unit 40 the implanted control unit 6 powers the motor 44 with energy from the battery 42, whereby the motor 44 operates the restriction device 4.

Figure 9:
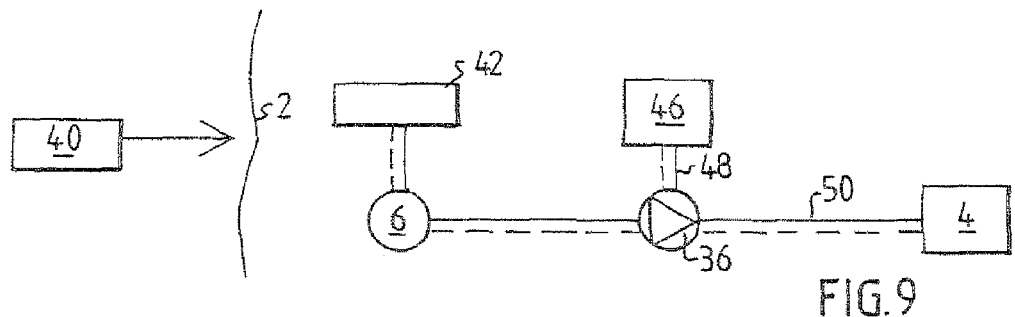

FIG. 9 shows an embodiment of the invention identical to that of FIG. 8, except that the motor/pump unit 36 of the embodiment of FIG. 7 is substituted for the motor 44 and a fluid reservoir 46 also is implanted in the patient. The reservoir 46 is via fluid conduits 48 and 50 connected to the motor/pump unit 36 and restriction device 4, which in this case is hydraulically operated. In response to a control signal from the external control unit 40, the implanted control unit 6 powers the electric motor of the motor/pump unit 36 with energy from the battery 42, whereby the motor/pump unit 36 distributes hydraulic fluid between the fluid reservoir 46 and the restriction device 4.

Figure 10:
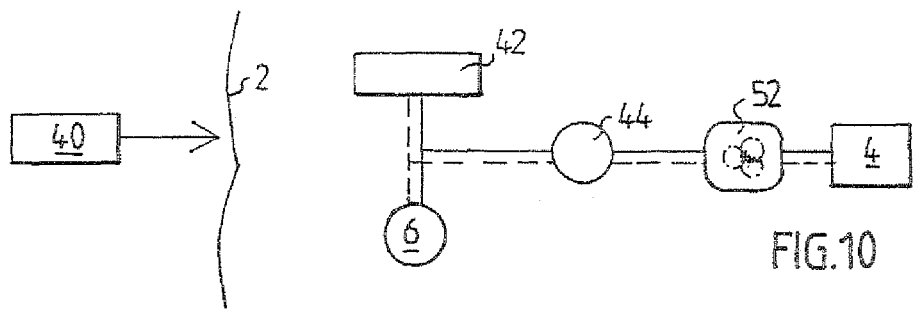

FIG. 10 shows an embodiment of the invention identical to that of FIG. 8, except that a mechanical reversing device in the form of a gearbox 52 also is implanted in the patient. The implanted control unit 6 controls the gearbox 52 to reverse the function performed by the restriction device 4 (mechanically operated).

Figure 11:
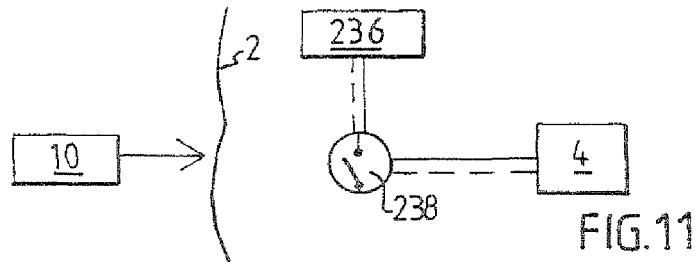
FIGS. 11 to 15 are schematic block diagrams illustrating five embodiments, respectively, of the invention, in which a switch is implanted in the patient for directly or indirectly switching the operation of the restriction device.

FIG. 11 shows an embodiment of the invention comprising the restriction device 4, the external control unit 10, an implanted source of energy 236 and an implanted switch 238. The switch 238 is operated by wireless energy released from the external source of energy of the external control unit 6 to switch between an off mode, in which the implanted source of energy 236 is not in use, and an on mode, in which the implanted source of energy 236 supplies energy for the operation of the restriction device 4.

Figure 12:
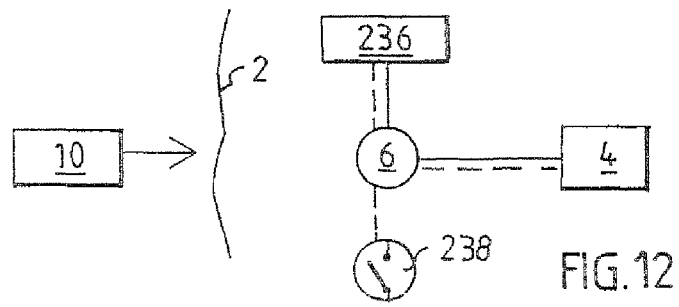

FIG. 12 shows an embodiment of the invention identical to that of FIG. 11, except that also the control unit 6 is implanted, in order to receive a control signal from the wireless remote control of the external control unit 10. The switch 238 is operated by the wireless energy from the external source of energy 10 to switch between an off mode, in which the implanted source of energy 236 and the wireless remote control of the external control unit 10 are not in use, i.e. the control unit 6 is not capable of receiving the control signal, and a standby mode, in which the wireless remote control is permitted to control the internal source of energy 236, via the implanted control unit 6, to supply energy for the operation of the restriction device 4.

Figure 13:
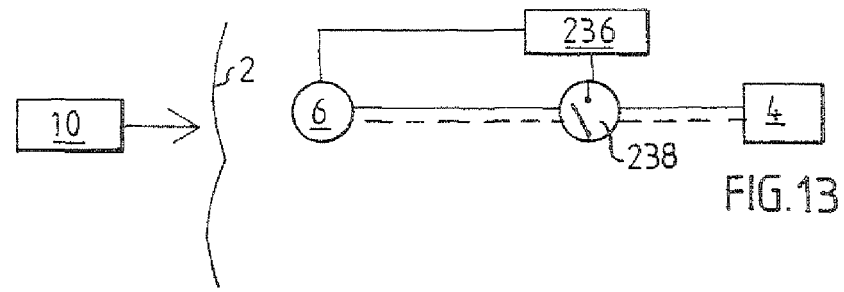

FIG. 13 shows an embodiment of the invention identical to that of FIG. 12, except that an energy transforming device for transforming the wireless energy into storable energy is incorporated in the implanted control unit 6 and that the implanted source of energy 236 is of a type that is capable of storing the storable energy. In this case, in response to a control signal from the external control unit 10, the implanted control unit 6 controls the switch 238 to switch from an off mode, in which the implanted source of energy 236 is not in use, to an on mode, in which the source of energy 36 supplies energy for the operation of the restriction device 4.

Figure 14:
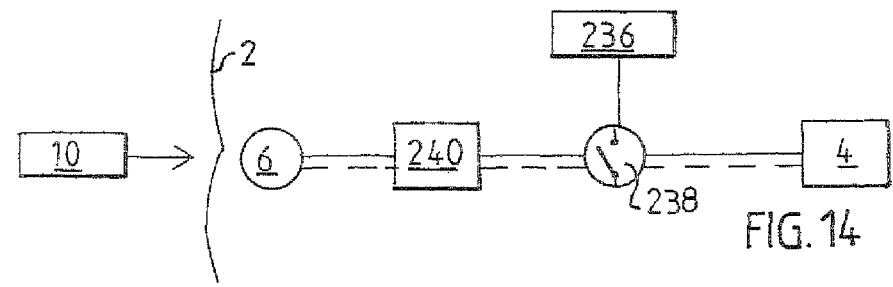

FIG. 14 shows an embodiment of the invention identical to that of FIG. 13, except that an energy storage device 240 also is implanted in the patient for storing the storable energy transformed from the wireless energy by the transforming device of the control unit 6. In this case, the implanted control unit 6 controls the energy storage device 240 to operate the switch 238 to switch between an off mode, in which the implanted source of energy 236 is not in use, and an on mode, in which the implanted source of energy 236 supplies energy for the operation of the restriction device 4.

Figure 15:
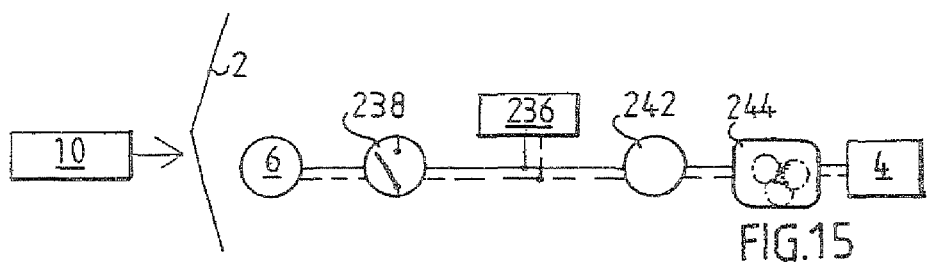

FIG. 15 shows an embodiment of the invention identical to that of FIG. 13, except that a motor 242 and a mechanical reversing device in the form of a gearbox 244 also are implanted in the patient. The implanted control unit 6 controls the gearbox 244 to reverse the function performed by the restriction device 4 (mechanically operated), i.e. enlarging and restricting the urine passageway.

Figure 16:
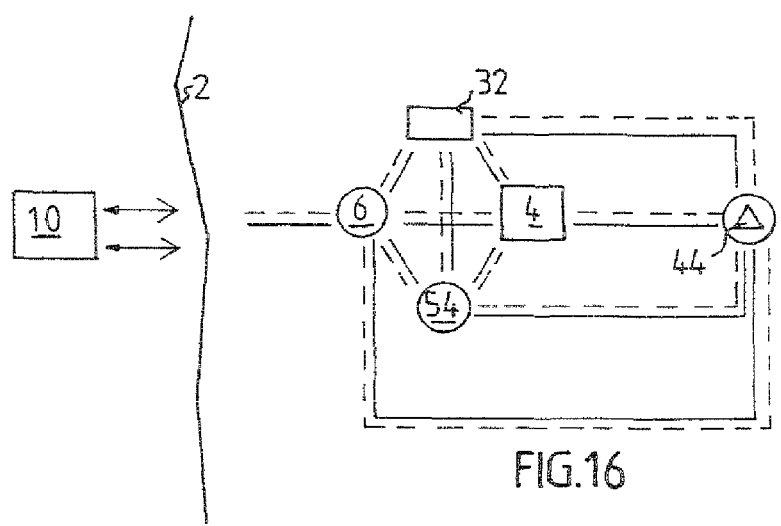
FIG. 16 is a schematic block diagram illustrating conceivable combinations of implantable components for achieving various communication options.

FIG. 16 schematically shows conceivable combinations of implanted components of the apparatus for achieving various communication possibilities. Basically, there are the implanted restriction device 4, the implanted control unit 6 and the external control unit 10 including the external source of energy and the wireless remote control. As already described above the remote control transmits a control signal generated by the external source of energy, and the control signal is received by a signal receiver incorporated in the implanted control unit 6, whereby the control unit 6 controls the implanted restriction device 4 in response to the control signal.

A sensor 54 may be implanted in the patient for sensing a physical parameter of the patient, such as the pressure in the stomach. The control unit 6, or alternatively the external control unit 10, may control the restriction device 4 in response to signals from the sensor 54. A transceiver may be combined with the sensor 54 for sending information on the sensed physical parameter to the external control unit 10. The wireless remote control of the external control unit 10 may comprise a signal transmitter or transceiver and the implanted control unit 6 may comprise a signal receiver or transceiver. Alternatively, the wireless remote control of the external control unit 10 may comprise a signal receiver or transceiver and the implanted control unit 6 may comprise a signal transmitter or transceiver. The above transceivers, transmitters and receivers may be used for sending information or data related to the restriction device from inside the patient's body to the outside thereof.

The motor 44 may be implanted for operating the restriction device 4 and also the battery 32 may be implanted for powering the motor 44. The battery 32 may be equipped with a transceiver for sending information on the charge condition of the battery.

Those skilled in the art will realize that the above various embodiments according to FIGS. 1-15 could be combined in many different ways. For example, the energy operated switch 14 could be incorporated in any of the embodiments of FIGS. 4,6,8-10. The hydraulic shifting device 38 could be incorporated in any of the embodiments of FIGS. 4 and 9. The gearbox 52 could be incorporated in any of the embodiments of FIGS. 1,6 and 8.

Figure 17:
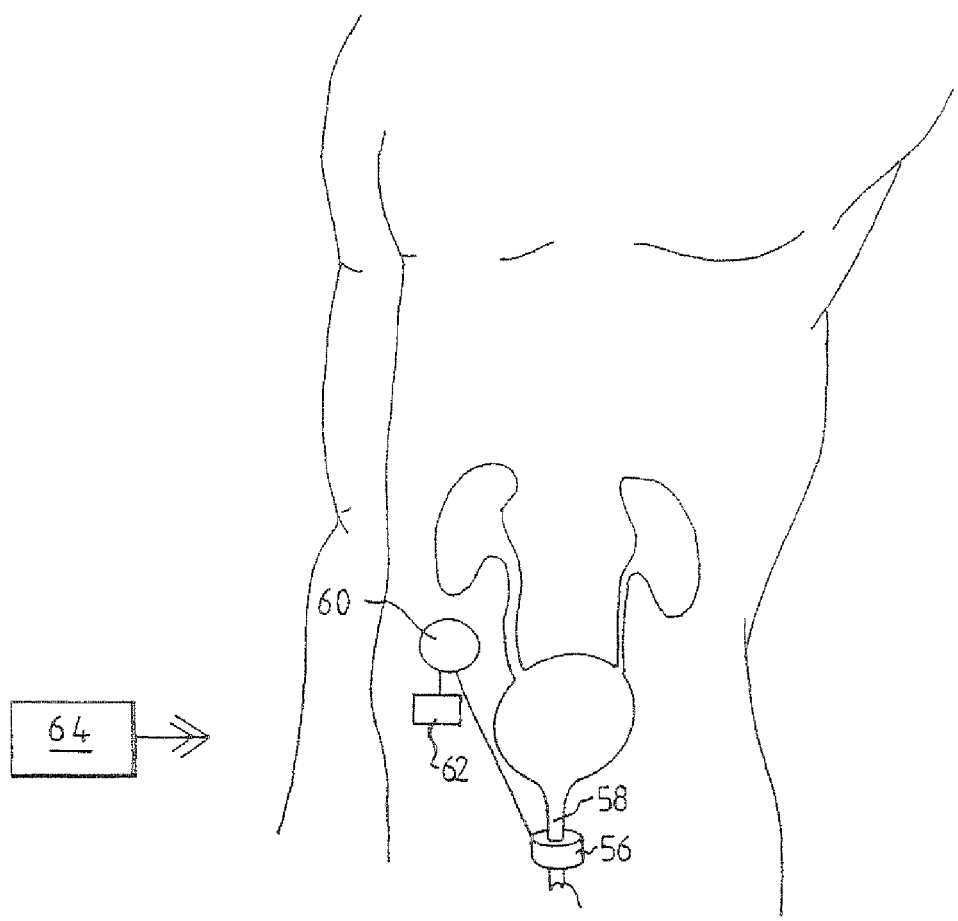
FIG. 17 illustrates the apparatus in accordance with the invention implanted in a patient.

FIG. 17 illustrates how any of the above-described embodiments of the apparatus of the invention may be implanted in a patient. Thus, an assembly of the apparatus implanted in the patient comprises a restriction device 56 engaging the urethra 58, an operation device 60 for operating the restriction device 56 and an internal control unit 62, which includes a signal receiver, for controlling the operation device 61. An external control unit 64 includes a signal transmitter for transmitting a wireless control signal to the signal receiver of the implanted control unit 62. The implanted control unit 62 is capable of transforming signal energy from the control signal into electric energy for powering the operation device 60 and for energizing energy consuming implanted components of the apparatus.

Figure 18:
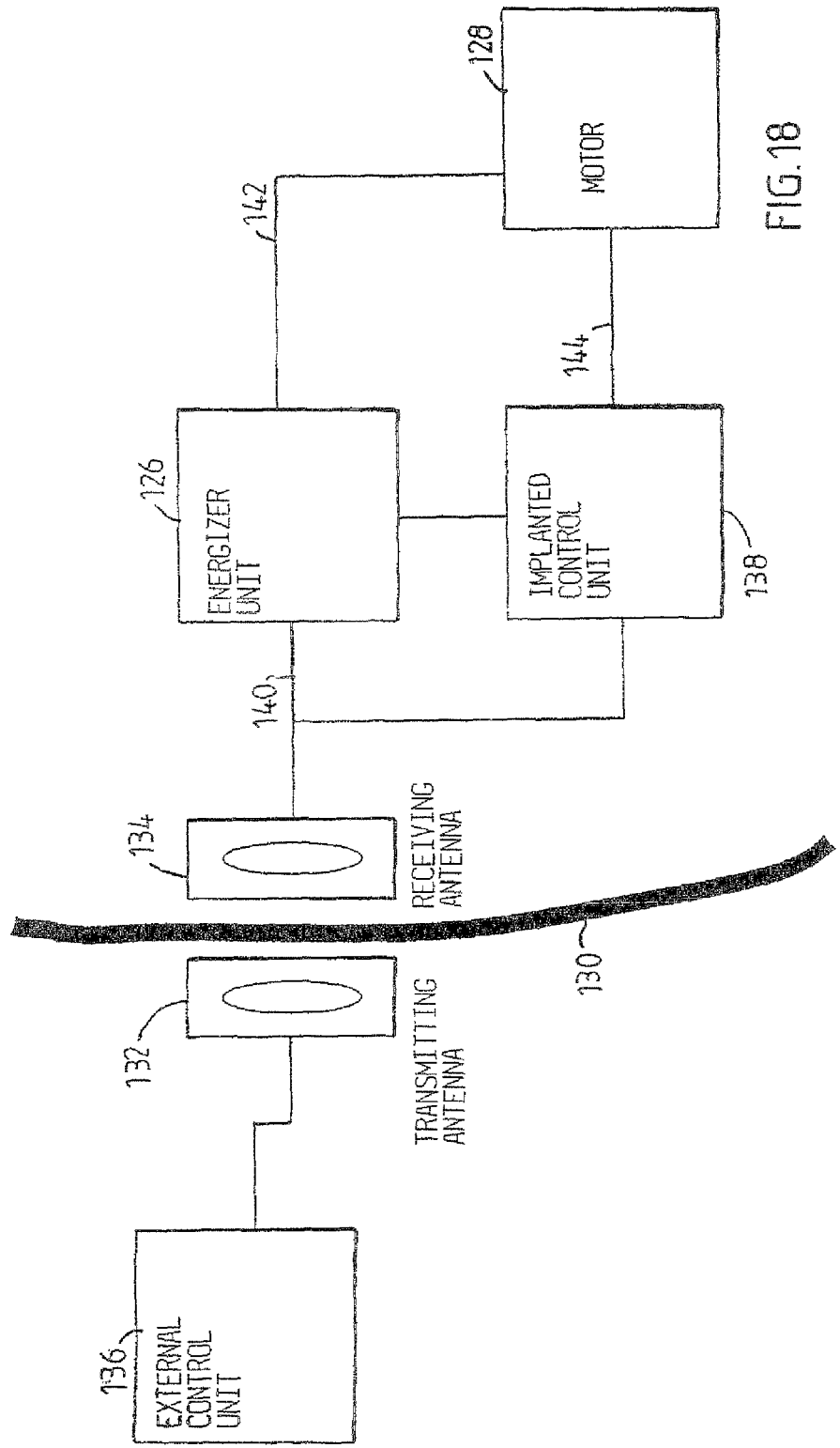
FIG. 18 is a block diagram illustrating remote control components of an embodiment of the invention.

FIG. 18 shows the basic parts of a wireless remote control of the apparatus of the invention including an electric motor 128 for operating a restriction device, for example of the type illustrated in FIG. 17. In this case, the remote control is based on the transmission of electromagnetic wave signals, often of high frequencies in the order of 100 kHz-1 gHz, through the skin 130 of the patient. In FIG. 18, all parts placed to the left of the skin 130 are located outside the patient's body and all parts placed to the right of the skin 130 are implanted. Any suitable remote control system may be used.

An external signal transmitting antenna 132 is to be positioned close to a signal receiving antenna, 134 implanted close to the skin 130. As an alternative, the receiving antenna 134 may be placed for example inside the abdomen of the patient. The receiving antenna 134 comprises a coil, approximately 1-100 mm, preferably 25 mm in diameter, wound with a very thin wire and tuned with a capacitor to a specific high frequency. A small coil is chosen if it is to be implanted under the skin of the patient and a large coil is chosen if it is to be implanted in the abdomen of the patient. The transmitting antenna 132 comprises a coil having about the same restriction as the coil of the receiving antenna 134 but wound with a thick wire that can handle the larger currents that is necessary. The coil of the transmitting antenna 132 is tuned to the same specific high frequency as the coil of the receiving antenna 134.

An external control unit 136 comprises a microprocessor, a high frequency electromagnetic wave signal generator and a power amplifier. The microprocessor of the control unit 136 is adapted to switch the generator on/off and to modulate signals generated by the generator to send digital information via the power amplifier and the antennas 132,134 to an implanted control unit 138. To avoid that accidental random high frequency fields trigger control commands, digital signal codes are used. A conventional keypad placed on the external control unit 136 is connected to the microprocessor thereof. The keypad is used to order the microprocessor to send digital signals to activate the restriction device to either restrict or enlarge the urine passageway. The microprocessor starts a command by applying a high frequency signal on the antenna 132. After a short time, when the signal has energized the implanted parts of the control system, commands are sent to restrict or enlarge the urine passageway in predefined steps. The commands are sent as digital packets in the form illustrated below.

| Start pattern, | Command, | Count, | Checksum, |
| 8 bits | 8 bits | 8 bits | 8 bits |

The commands are sent continuously during a rather long time period (e.g. about 30 seconds or more). When a new restrict or enlarge step is desired the Count byte is increased by one to allow the implanted control unit 138 to decode and understand that another step is demanded by the external control unit 136. If any part of the digital packet is erroneous, its content is simply ignored.

Through a line 140, an implanted energizer unit 126 draws energy from the high frequency electromagnetic wave signals received by the receiving antenna 134. The energizer unit 126 stores the energy in a power supply, such as a large capacitor, powers the control unit 138 and powers the electric motor 128 via a line 142.

The control unit 138 comprises a demodulator and a microprocessor. The demodulator demodulates digital signals sent from the external control unit 136. The microprocessor of the control unit 138 receives the digital packet, decodes it and, provided that the power supply of the energizer unit 126 has sufficient energy stored, sends a signal via a signal line 144 to the motor 128 to either contract or enlarge the restriction device depending on the received command code.

Alternatively, the energy stored in the power supply of the energizer unit may only be used for powering a switch, and the energy for powering the motor 128 may be obtained from another implanted power source of relatively high capacity, for example a battery. In this case the switch is adapted to connect said battery to the control unit 138 in an on mode when said switch is powered by said power supply and to keep said battery disconnected from the control unit in a standby mode when said switch is unpowered.

Figure 19:
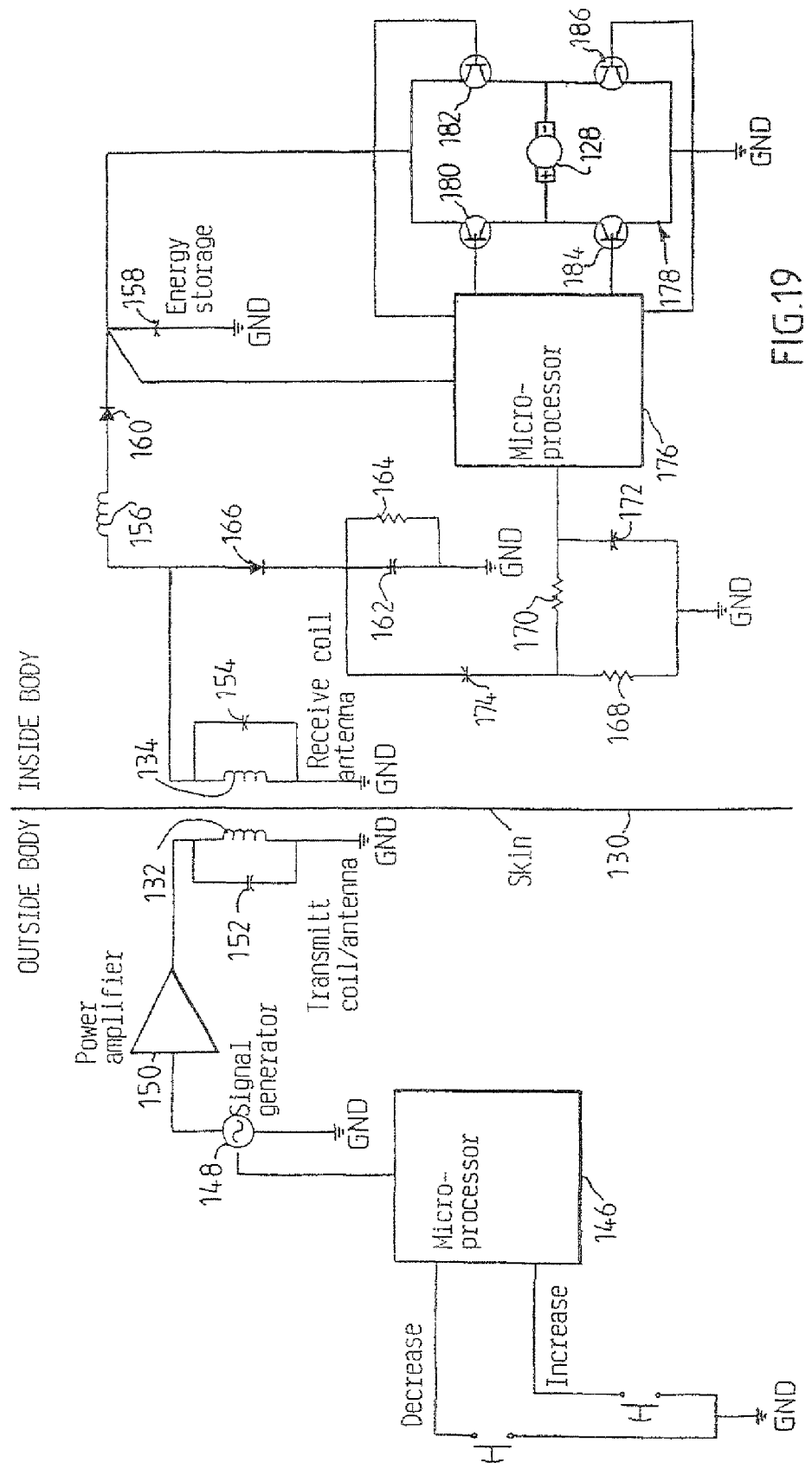
FIG. 19 is a schematic view of exemplary circuitry used for the components of the block diagram of FIG. 18.

With reference to FIG. 19, the remote control schematically described above will now be described in accordance with a more detailed embodiment. The external control unit 136 comprises a microprocessor 146, a signal generator 148 and a power amplifier 150 connected thereto. The microprocessor 146 is adapted to switch the signal generator 148 on/off and to modulate signals generated by the signal generator 148 with digital commands that are sent to implanted components of the apparatus. The power amplifier 150 amplifies the signals and sends them to the external signal transmitting antenna 132. The antenna 132 is connected in parallel with a capacitor 152 to form a resonant circuit tuned to the frequency generated by the signal generator 148.

The implanted signal receiving antenna coil 134 forms together with a capacitor 154 a resonant circuit that is tuned to the same frequency as the transmitting antenna 132. The signal receiving antenna coil 134 induces a current from the received high frequency electromagnetic waves and a rectifying diode 160 rectifies the induced current, which charges a storage capacitor 158. A coil 156 connected between the antenna coil 134 and the diode 160 prevents the capacitor 158 and the diode 160 from loading the circuit of the signal receiving antenna 134 at higher frequencies. Thus, the coil 156 makes it possible to charge the capacitor 158 and to transmit digital information using amplitude modulation.

A capacitor 162 and a resistor 164 connected in parallel and a diode 166 forms a detector used to detect amplitude modulated digital information. A filter circuit is formed by a resistor 168 connected in series with a resistor 170 connected in series with a capacitor 172 connected in series with the resistor 168 via ground, and a capacitor 174, one terminal of which is connected between the resistors 168,170 and the other terminal of which is connected between the diode 166 and the circuit formed by the capacitor 162 and resistor 164. The filter circuit is used to filter out undesired low and high frequencies. The detected and filtered signals are fed to an implanted microprocessor 176 that decodes the digital information and controls the motor 128 via an H-bridge 178 comprising transistors 180,182,184 and 186. The motor 128 can be driven in two opposite directions by the H-bridge 178.

The microprocessor 176 also monitors the amount of stored energy in the storage capacitor 158. Before sending signals to activate the motor 128, the microprocessor 176 checks whether the energy stored in the storage capacitor 158 is enough. If the stored energy is not enough to perform the requested operation, the microprocessor 176 waits for the received signals to charge the storage capacitor 158 before activating the motor 128.

The invention claimed is:

1. An urinary incontinence treatment apparatus, comprising a restriction device implantable in a patient suffering from urinary incontinence for engaging the urethra or urine bladder to form a restricted urine passageway in the urethra or urine bladder, the restriction device being operable to change the restriction of the urine passageway,
   a source of energy, and
   a control device operable from outside the patient's body for controlling the source of energy to release energy for use in connection with the operation of the restriction device,
   a powered operation device implantable in the patient, wherein the source of energy is adapted to power the powered operation device, and the control device is adapted to control the operation device to operate the restriction device, characterized in that the apparatus further comprises:
   an external data communicator intended to be outside the patient's body, and
   an internal data communicator implantable in the patient for communicating with the external communicator, wherein the internal data communicator feeds data related to the patient, or related to the restriction device, back to the external data communicator.

2. An apparatus according to claim 1, wherein the source of energy is intended to be external to the patient's body when the restriction device is implanted therein, and the control device is adapted to control the external source of energy to release wireless energy for use in connection with the operation of the restriction device.

3. The apparatus according to claim 2, wherein the control device is adapted to control the external source of energy to release wireless energy for direct use in connection with the operation of the restriction device.

4. An apparatus according to claim 3, further comprising motor or a pump implantable in the patient for operating the restriction device, wherein the wireless energy directly or indirectly powers the motor or the pump.

5. An apparatus according to claim 3, further comprising an activatable source of energy implantable in the patient, wherein the implantable source of energy is activated by wireless energy released from the external source of energy, to supply energy which is used in connection with the operation of the restriction device.

6. The apparatus according to claim 2, wherein the control device is adapted to control the external source of energy to intermittently release wireless energy in the form of a train of energy pulses for direct use in connection with the operation of the restriction device.

7. An apparatus according to claim 6, wherein the control device is adapted to control the source of energy to release electric energy, and further comprising an implantable capacitor for producing the train of energy pulses from the released energy.

8. An apparatus according to claim 7, further comprising an implantable capacitor or accumulator, wherein the charge or discharge of the capacitor or accumulator is controlled by use of the voltage level guard.

9. An apparatus according to claim 2, further comprising an energy storage device implantable in the patient for storing the wireless energy released from the external source of energy.

10. An apparatus according to claim 9, wherein the energy storage device comprises an accumulator.

11. An apparatus according to claim 10, wherein the accumulator comprises an electric accumulator.

12. An apparatus according to claim 11, wherein the electric accumulator comprises at least one capacitor or at least one rechargeable battery, or a combination of at least one capacitor and at least one rechargeable battery.

13. An apparatus according to claim 2, further comprising a battery implantable in the patient for supplying electric energy to implantable electric energy consuming components of the apparatus.

14. An apparatus according to claim 2, further comprising an implantable stabilizer for stabilizing the energy released by the control device.

15. An apparatus according to claim 14, wherein the energy released by the control device comprises electric energy and the stabilizer comprises at least one capacitor.

16. An apparatus according to claim 14, wherein the released energy comprises electric energy and further comprising an implantable capacitor for producing the train of energy pulses.

17. An apparatus according to claim 14, wherein the capacitor has a capacity less than 0.1 µF.

18. An apparatus according to claim 2, further comprising implantable electrical components including at least one voltage level guard.

19. An apparatus according to claim 18, wherein the electrical components are devoid of any current detector and/or charge level detector.

20. An apparatus according to claim 2, further comprising implantable electrical components including a single voltage level guard.

21. An apparatus according to claim 2, wherein the control device is adapted to release wireless energy in the form of a magnetic field or electromagnetic waves for direct power of the motor or pump, as the wireless energy is being released.

22. An apparatus according to claim 21, wherein the pump is not a plunger type of pump.

23. An apparatus according to claim 1, wherein the restriction device is operable by the released energy in a manual, mechanical, thermal or magnetic manner.

24. An apparatus according to claim 1, wherein the powered operation device comprises a motor or a pump.

25. An apparatus according to claim 24, wherein the operation device is powered by magnetic energy, non-magnetic energy, electromagnetic energy, non-electromagnetic energy, kinetic energy, non-kinetic energy, thermal energy or non-thermal energy.

26. An apparatus according to claim 24, wherein the operation device comprises an electrical operation device.

27. An apparatus according to claim 24, wherein the control device controls the operation device to operate the restriction device.

28. An apparatus according to claim 27, wherein the operation device comprises hydraulic means and at least one valve for controlling a fluid flow in the hydraulic means.

29. An apparatus according to claim 28, wherein the control device comprises a wireless remote control for controlling the valve.

30. An apparatus according to claim 27, wherein the restriction device comprises hydraulic means and the operation device comprises a reservoir forming a fluid chamber with a variable volume connected to the hydraulic means, and the operation device is adapted to distribute fluid from the chamber to the hydraulic means by reduction of the volume of the chamber and to withdraw fluid from the hydraulic means to the chamber by expansion of the volume of the chamber.

31. An apparatus according to claim 24, wherein the operation device comprises a motor.

32. An apparatus according to claim 31, wherein the motor comprises a rotary motor, and the control device controls the rotary motor to rotate a desired number of revolutions.

33. An apparatus according to claim 31, wherein the motor comprises a linear motor.

34. An apparatus according to claim 31, wherein the motor comprises a hydraulic or pneumatic fluid motor, and the control device controls the fluid motor.

35. An apparatus according to claim 31, wherein the motor comprises an electric motor having electrically conductive parts made of plastics.

36. An apparatus according to claim 24 wherein the restriction device comprises hydraulic means and the operation device is adapted to conduct a hydraulic fluid in the hydraulic means.

37. An apparatus according to claim 36, wherein the operation device comprises a motor.

38. An apparatus according to claim 36, wherein the operation device comprises a fluid conduit connected to the hydraulic means of the restriction device, and a reservoir for hydraulic fluid, the reservoir forming part of the conduit.

39. An apparatus according to claim 38, wherein the hydraulic means and conduit is devoid of any non-return valve.

40. An apparatus according to claim 39, wherein the reservoir forms a fluid chamber with a variable volume, and the operation device is adapted to distribute fluid from the chamber to the hydraulic means of the restriction device by reduction of the volume of the chamber and to withdraw fluid from the hydraulic means to the chamber by expansion of the volume of the chamber.

41. An apparatus according to claim 1, wherein the control device is activated in a manual or non-manual manner to control the source of energy to release energy.

42. An apparatus according to claim 1, further comprising an adjustment device for adjusting the restriction device to change the restriction of the urine passageway, wherein the adjustment device is adapted to mechanically adjust the restriction device, or adapted to hydraulically adjust the restriction device by using hydraulic means which is devoid of hydraulic fluid of the kind having a viscosity that substantially increases when exposed to heat or a magnetic field.

43. An apparatus according to claim 1, wherein the control device is adapted to control the restriction device.

44. An apparatus according to claim 43, wherein the control device comprises an internal control unit implantable in the patient for controlling the restriction device.

45. An apparatus according to claim 44, wherein the internal control unit is programmable.

46. An apparatus according to claim 45, wherein the control device comprises an external control unit intended to be outside the patient's body, the internal control unit being programmable by the external control unit.

47. An apparatus according to claim 46, wherein the external control unit loads the internal control unit with data in accordance with a loading mode only authorized for a doctor.

48. An apparatus according to claim 46, wherein the external control unit controls the internal control unit in accordance with a doctor mode only authorized for a doctor.

49. An apparatus according to claim 46, wherein the external control unit controls the internal control unit in accordance with a patient mode permitted for the patient.

50. An apparatus according to claim 45, wherein the internal control unit is programmable for controlling the restriction device over time.

51. An apparatus according to claim 50, wherein the internal control unit controls the restriction device over time in accordance with an activity schedule program.

52. An apparatus according to claim 50, wherein the internal control unit comprises a microprocessor.

53. The apparatus according to claim 43, wherein the control device comprises a wireless remote control.

54. An apparatus according to claim 1, wherein the source of energy is implantable in the patient.

55. An apparatus according to claim 54, wherein the implantable source of energy comprises at least one accumulator, at least one capacitor or at least one rechargeable battery, or a combination of at least one capacitor and at least one rechargeable battery.

56. An apparatus according to claim 55, wherein the implantable source of energy comprises an electric source of energy.

57. An apparatus according to claim 56, wherein the electric source of energy comprises an accumulator, or a battery having a lifetime of at least 10 years.

58. The apparatus according to claim 54, further comprising an energy transforming device implantable in the patient for transforming the wireless energy into storable energy, wherein the internal source of energy is capable of storing the storable energy.

59. The apparatus according to claim 58, wherein the switch switches from an "off" mode, in which the internal source of energy is not in use, to an "on" mode, in which the source of energy supplies energy for the operation of the restriction device.

60. The apparatus according to claim 59, wherein the control device controls the switch to switch between the "on" and "off" modes.

61. The apparatus according to claim 60, wherein the control device comprises a wireless remote control.

62. An apparatus according to claim 60, wherein the control device shifts polarity of the released energy to reverse the operation device.

63. An apparatus according to claim 60, wherein the operation device comprises an electric motor and the released energy comprises electric energy.

64. An apparatus according to claim 54, wherein the wireless energy comprises electromagnetic waves excluding radio waves.

65. The apparatus according to claim 1, further comprising a switch implantable in the patient for directly or indirectly switching the operation of the restriction device.

66. The apparatus according to claim 65, further comprising an internal source of energy implantable in the patient for supplying energy for the operation of the restriction device, wherein the switch directly or indirectly affects the supply of energy from the internal source of energy.

67. The apparatus according to claim 66, wherein the switch switches between an "off" mode, in which the internal source of energy is not in use, and an "on" mode, in which the internal source of energy supplies energy for the operation of the restriction device.

68. The apparatus according to claim 67, wherein the switch is operable by the wireless energy released from the external source of energy.

69. The apparatus according to claim 68, wherein the control device controls the external source of energy to release the wireless energy.

70. The apparatus according to claim 66, wherein the control device comprises a wireless remote control for controlling the internal source of energy.

71. The apparatus according to claim 70, further comprising a switch operable by the wireless energy from the external source of energy to switch between an "off" mode, in which the internal source of energy and remote control are not in use, and a "standby" mode, in which the remote control is permitted to control the internal source of energy to supply energy for the operation of the restriction device.

72. The apparatus according to claim 66, further comprising an energy transforming device implantable in the patient for transforming the wireless energy into storable energy and an energy storage device implantable in the patient for storing the storable energy.

73. The apparatus according to claim 72, wherein the switch is operable by energy from the implantable energy storage device to switch between an "off" mode, in which the internal source of energy is not in use, and an "on" mode, in which the internal source of energy supplies energy for the operation of the restriction device.

74. The apparatus according to claim 73, wherein the control device controls the energy storage device to operate the switch.

75. The apparatus according to claim 66, wherein the internal source of energy comprises an electric source of energy.

76. The apparatus according to claim 75, wherein the electric source of energy comprises at least one accumulator, at least one capacitor or at least one rechargeable battery, or a combination of at least one capacitor and at least one rechargeable battery.

77. The apparatus according to claim 75, wherein the electric source of energy comprises an accumulator or a battery having a lifetime of at least 10 years.

78. The apparatus according to claim 1, wherein the control device comprises a wireless remote control.

79. The apparatus according to claim 1, wherein the source of energy comprises a nuclear source of energy.

80. The apparatus according to claim 1, wherein the source of energy comprises a chemical source of energy.

81. An apparatus according to claim 1, wherein the control device releases polarized energy from the source of energy.

82. An apparatus according to claim 1, wherein the restriction device is operable to perform a reversible function.

83. An apparatus according to claim 82, further comprising a reversing device implantable in the patient for reversing the function performed by the restriction device.

84. An apparatus according to claim 83, wherein the control device controls the reversing device to reverse the function performed by the restriction device.

85. An apparatus according to claim 83, wherein the reversing device comprises hydraulic means including a valve for shifting the flow direction of a fluid in the hydraulic means.

86. An apparatus according to claim 83, wherein the reversing device comprises a mechanical reversing device.

87. An apparatus according to claim 86, wherein the mechanical reversing device comprises a switch.

88. An apparatus according to claim 86, wherein the reversing device comprises a gearbox.

89. An apparatus according to claim 83, wherein the reversing device comprises a switch.

90. An apparatus according to claim 89, wherein the switch of the reversing device is operable by the released energy.

91. An apparatus according to claim 90, wherein the control device controls the operation of the switch of the reversing device by shifting polarity of the released energy supplied to the switch.

92. An apparatus according to claim 89, wherein the switch comprises an electric switch and the source of energy supplies electric energy for the operation of the switch.

93. An apparatus according to claim 89, wherein the operation device comprises a motor, and the reversing device reverses the motor.

94. An apparatus according to claim 1, further comprising at least one implantable sensor for sensing at least one physical parameter of the patient.

95. An apparatus according to claim 94, wherein the sensor comprises a pressure sensor for directly or indirectly sensing as the physical parameter the pressure in the urethra or urine bladder.

96. An apparatus according to claim 94, wherein the control device controls the restriction device in response to signals from the sensor.

97. An apparatus according to claim 96, wherein the control device comprises an internal control unit implantable in the patient, the internal control unit controlling the restriction device in response to signals from the sensor.

98. An apparatus according to claim 97, wherein the control device comprises an external control unit outside the patient's body, the external control unit controlling the restriction device in response to signals from the sensor.

99. An apparatus according to claim 98, wherein the external control unit stores information on the physical parameter sensed by the sensor and is manually operated to control the restriction device based on the stored information.

100. An apparatus according to claim 94, further comprising at least one implantable sender for sending information on the physical parameter sensed by the sensor.

101. An apparatus according to claim 1, wherein the external data communicator feeds data to the internal data communicator.

102. An apparatus according to claim 101, wherein the internal data communicator feeds data related to the restriction device.

103. An apparatus according to claim 101, wherein the implantable communicator feeds data related to at least one physical signal of the patient.

104. An apparatus according to claim 1, wherein the restriction device is adapted to control the restriction of the urine passageway.

105. An apparatus according to claim 104, wherein the restriction device is operable to enlarge and restrict the urine passageway when implanted in the patient.

106. An apparatus according to claim 104, wherein the restriction device is adapted to steplessly control the restriction of the urine passageway when implanted in the patient.

107. An apparatus according to claim 1, further comprising an implantable energy transforming device, wherein the control device is adapted to control the source of energy to release wireless electric energy, and the energy transforming device is adapted to transform the electric energy into kinetic energy for operation of the restriction device.

108. An apparatus according to claim 107, wherein the restriction device is directly operated with the kinetic energy, as the energy transforming device transforms the electric energy into the kinetic energy.

109. An apparatus according to claim 1, wherein the control device controls the source of energy to release magnetic energy, non-magnetic energy, electromagnetic energy, non-electromagnetic energy, kinetic energy, non-kinetic energy, sonic energy, non-sonic energy, thermal energy or non-thermal energy.

110. An apparatus according to claim 1, wherein the restriction device is non-inflatable.

111. An apparatus according to claim 1, wherein the control device controls the source of energy to release energy for a determined time period.

112. An apparatus according to claim 1, wherein the control device controls the source of energy to release energy in a determined number of energy pulses.

113. An apparatus according to claim 1, wherein the control device is adapted to control the source of energy to release energy in a non-invasive manner.

114. An apparatus according to claim 1, wherein the control device comprises a wireless remote control for transmitting at least one wireless control signal for controlling the restriction device.

115. An apparatus according to claim 114, wherein the remote control is capable of obtaining information on the condition of the restriction device when the restriction device is implantable and to control the restriction device in response to the information.

116. An apparatus according to any of claim 115, wherein the remote control transmits a carrier signal for carrying the control signal.

117. An apparatus according to claim 116, wherein the carrier signal is frequency, amplitude or frequency and amplitude modulated.

118. An apparatus according to claim 116, wherein the carrier signal is digital, analog or digital and analog.

119. An apparatus according to claim 118, wherein the control signal used with the carrier signal is frequency, amplitude or frequency and amplitude modulated.

120. An apparatus according to claim 114, wherein the wireless remote control comprises at least one external signal transmitter or transceiver and at least one internal signal receiver or transceiver implantable in the patient.

121. An apparatus according to claim 114, wherein the wireless remote control comprises at least one external signal receiver or transceiver and at least one internal signal transmitter or transceiver implantable in the patient.

122. An apparatus according to claim 114, wherein the remote control is capable of sending information related to the restriction device from inside the patient's body to the outside thereof.

123. An apparatus according to claim 122, wherein the remote control controls the restriction device in response to the information.

124. An apparatus according to claim 114, wherein the control signal comprises a wave signal comprising one of a sound wave signal including an ultrasound wave signal, an electromagnetic wave signal including an infrared light signal, a visible light signal, an ultra violet light signal and a laser light signal, a micro wave signal, a radio wave signal, an x-ray radiation signal, and a gamma radiation signal.

125. An apparatus according to claim 124, wherein the control signal is transmitted in pulses by the wireless remote control.

126. An apparatus according claim 114, wherein the control signal comprises an electric, magnetic or electric and magnetic field.

127. An apparatus according to claim 114, wherein the control signal is digital, analog or digital and analog.

128. An apparatus according to claim 127, wherein the remote control transmits an electromagnetic carrier wave signal for carrying the digital or analog control signal.

129. An apparatus according to claim 1, wherein the control device is adapted to control the source of energy to release energy for direct use in connection with the operation of the restriction device.

130. An apparatus according to claim 1, wherein the control device is adapted to control the source of energy to intermittently release energy in the form of a train of energy pulses for direct use in connection with the operation of the restriction device.

131. An apparatus according to claim 1, wherein the control device is adapted to control the source of energy to directly power the motor or pump with the released energy.

132. An apparatus according to claim 1 wherein the wireless energy comprises a signal.

133. An apparatus according to claim 1, further comprising an implantable energy transforming device for transforming wireless energy directly or indirectly into energy different than the wireless energy for operation of the restriction device.

134. An apparatus according to claim 133, wherein the energy transforming device transforms the wireless energy in the form of sound waves into electric energy for operation of the restriction device.

135. An apparatus according to claim 134, wherein the energy transforming device transforms the wireless energy in the form of sound waves directly into electric energy.

136. An apparatus according to any of claim 134, wherein the energy transforming device comprises a capacitor.

137. An apparatus according to claim 136, wherein the capacitor is adapted to produce electric pulses from the transformed electric energy.

138. An apparatus according to claim 133, wherein the operation device comprises an implantable motor or pump for operating the restriction device, wherein the motor or pump is powered by the transformed energy.

139. An apparatus according to claim 1, wherein the restriction device is adjustable in a non-manual manner.

140. An apparatus according to claim 1, wherein the restriction device is embedded in a soft or gel-like material.

141. An apparatus according to claim 1, wherein the restriction device is embedded in a silicone material having hardness less than 20 Shore.

142. An apparatus according to claim 1, wherein the operation device comprises a motor or a pump, and wherein the control device is adapted to control the motor or pump by releasing energy to operate the motor or to operate the restriction to both restrict the urine passageway and reverse the function performed by the restriction device.

* * * * *